US006858595B2

(12) United States Patent
Hayes et al.

(10) Patent No.: US 6,858,595 B2
(45) Date of Patent: Feb. 22, 2005

(54) USE OF BIOLOGICALLY ACTIVE VITAMIN D COMPOUNDS FOR THE PREVENTION AND TREATMENT OF INFLAMMATORY BOWEL DISEASE

(75) Inventors: Colleen E. Hayes, Madison, WI (US); Faye E. Nashold, Sun Prairie, WI (US)

(73) Assignee: Wisconsin Alumni Research Association, Madison, WI (US)

( * ) Notice: Subject to any disclaimer, the term of this patent is extended or adjusted under 35 U.S.C. 154(b) by 0 days.

(21) Appl. No.: 10/036,819

(22) Filed: Dec. 21, 2001

(65) Prior Publication Data

US 2002/0128241 A1 Sep. 12, 2002

Related U.S. Application Data

(63) Continuation of application No. 09/469,985, filed on Dec. 21, 1999, now Pat. No. 6,358,939.

(51) Int. Cl.[7] .................. A61K 31/59; C07C 401/00
(52) U.S. Cl. ......................... 514/167; 552/653
(58) Field of Search .................. 514/167; 552/653; 424/439, 442, 451, 464, 465, 400

(56) References Cited

U.S. PATENT DOCUMENTS

| 4,312,806 | A | | 1/1982 | Lambert et al. ............ 260/149 |
|---|---|---|---|---|
| 4,638,043 | A | * | 1/1987 | Szycher et al. ............. 528/75 |
| 5,216,002 | A | | 6/1993 | Gidda et al. ............... 514/369 |
| 5,238,931 | A | | 8/1993 | Yoshikawa et al. ......... 514/184 |
| 5,294,630 | A | | 3/1994 | Blake et al. ............... 514/372 |
| 5,368,854 | A | | 11/1994 | Rennick ..................... 424/852 |
| 5,391,555 | A | | 2/1995 | Marshall et al. ............ 514/311 |
| 5,446,035 | A | | 8/1995 | Neef et al. ................. 514/167 |
| 5,506,213 | A | | 4/1996 | Carson et al. ............... 514/46 |
| 5,518,725 | A | * | 5/1996 | Daynes et al. .......... 424/212.1 |
| 5,552,439 | A | | 9/1996 | Panetta ...................... 514/534 |
| 5,569,680 | A | | 10/1996 | Wu ........................... 514/786 |
| 5,583,125 | A | | 12/1996 | Steinmeyer et al. | |
| 5,643,602 | A | * | 7/1997 | Ulmius ....................... 424/462 |
| 5,663,157 | A | | 9/1997 | Steinmeyer et al. | |
| 5,710,142 | A | | 1/1998 | Calverley et al. ........... 514/167 |
| 5,711,964 | A | * | 1/1998 | Dattagupta et al. ......... 424/450 |
| 5,716,945 | A | | 2/1998 | Grue-Sorensen ............ 514/167 |
| 5,716,946 | A | | 2/1998 | De Luca et al. ............. 514/167 |
| 5,756,449 | A | | 5/1998 | Andersen et al. .............. 514/8 |
| 5,756,733 | A | | 5/1998 | Hesse et al. ................. 544/164 |
| 5,786,347 | A | | 7/1998 | Hesse et al. ................. 516/167 |
| 5,792,795 | A | | 8/1998 | Buser et al. ................. 514/560 |

(List continued on next page.)

FOREIGN PATENT DOCUMENTS

| DE | 44 05 545 | 8/1995 |
|---|---|---|
| EP | 0927721 | 12/1997 |
| WO | WO 96/30326 | 10/1996 |
| WO | WO 98/51644 | 11/1998 |
| WO | WO 98/51678 | 11/1998 |
| WO | WO 01/42205 A2 | 6/2001 |

OTHER PUBLICATIONS

Tada, M. et al. (DN BA81:48751, BIOSIS, abstract of J. Jpn Soc. Colo–Proctol, (1985), 38 (6), 663–668).*
Barrat et al. (DN 136:339213, CAPLUS, abstract of J. of Experimental Medicine (2002), 195(5), 603–616).
Penna et al. (DN 132:292680, CAPLUS, abstract of J. of Immunology (2000), 164(5), 2405–2411).

(List continued on next page.)

Primary Examiner—Sabiha N. Qazi
(74) Attorney, Agent, or Firm—Foley & Lardner LLP

(57) ABSTRACT

Methods of treating inflammatory bowel disease are described, and in particular the prevention and treatment of inflammatory bowel disease in humans as well as other animals. These methods involve the administration of biologically active vitamin D compounds, and therapeutic compositions thereof, so that the symptoms of Inflammatory Bowel Disease are reduced or relieved.

16 Claims, 2 Drawing Sheets

U.S. PATENT DOCUMENTS

| | | | | |
|---|---|---|---|---|
| 5,811,562 A | | 9/1998 | Hesse et al. | 552/653 |
| 5,824,313 A | * | 10/1998 | Daynes et al. | 424/184.1 |
| 5,830,505 A | * | 11/1998 | Fischer et al. | 424/487 |
| 5,834,016 A | * | 11/1998 | Naeff et al. | 424/450 |
| 5,834,021 A | | 11/1998 | Speirs | 424/490 |
| 5,851,548 A | * | 12/1998 | Dattagupta et al. | 424/450 |
| 5,872,140 A | | 2/1999 | Hesse et al. | 514/359 |
| 5,876,746 A | * | 3/1999 | Jona et al. | 424/449 |
| 5,877,168 A | | 3/1999 | Miyamoto et al. | 514/167 |
| 5,883,271 A | | 3/1999 | Ono | 552/653 |
| 5,888,969 A | | 3/1999 | Girten et al. | 514/8 |
| 5,889,028 A | | 3/1999 | Sandborn et al. | 514/343 |
| 5,891,865 A | | 4/1999 | De Luca et al. | 514/167 |
| 5,902,806 A | | 5/1999 | Ikeda et al. | 514/167 |
| 5,905,074 A | | 5/1999 | Schneider | 514/167 |
| 5,929,056 A | | 7/1999 | Mourino et al. | 514/167 |
| 5,932,214 A | | 8/1999 | Lobb et al. | 424/144.1 |
| 5,932,565 A | | 8/1999 | Grue-Sorensen | 514/167 |
| 5,936,105 A | | 8/1999 | Paaren | 552/653 |
| 5,952,317 A | | 9/1999 | De Luca et al. | 514/167 |
| 5,981,597 A | * | 11/1999 | Wu | 514/616 |
| 6,214,373 B1 | * | 4/2001 | Snowden | 424/439 |
| 6,440,953 B1 | * | 8/2002 | DeLuca et al. | 514/167 |
| 2003/0188756 A1 | * | 10/2003 | Cantoma | 128/898 |

OTHER PUBLICATIONS

Darn et al. (DN 132:146376, CAPLUS, abstract of J. of Investigative Dermatology (1999), 113(6), 1082–1089).

Bemiss, C. J. et al., "Interleukin–2 is one of the targets of 1,25–dihydroxyvitamin D3 in the immune system," *Archives of Biochemistry and Biophysics,* 402 (2002), pp. 249–254; published by Elsevier Science (USA).

Bickston, S.J. et al., "Recombinant Interleukin 10 for the Treatment of Active Crohn's Disease: Lessons in Biologic Therapy," *Gastroenterology,* 119 (6) (2000), pp. 1781–1783; published by American Gastroenterological Association (USA).

Cantorna, M. T. et al., "1,25–Dihydroxycholecalciferol Prevents and Ameliorates Symptoms of Experimental Murine inflammatory Bowel Disease," *J. Nutr.,* 130 (2000), pp. 2648–2652; published by American Society for Nutritional Sciences (USA).

Colombel, J–F. et al., "Interleukin 10 (Tenovil) in the prevention of postoperative recurrence of Crohn's disease," *Gut,* 49 (2001) pp. 42–46; published by British Medical Association (United Kingdom).

Cornillie, F. et al., "Infliximab induces potent anti–inflammatory and local immunomodulatory activity but no systemic immune suppression in patients with Crohn's disease," *Aliment Pharmacol Ther.,* 15 (2001), pp. 463–473; published by Blackwell Science Ltd.

Fedorak, R. N. et al., "Recombinant Human Interleukin 10 in the Treatment of Patients with Mild to Moderately Active Crohn's Disease," *Gastroenterology,* 119 (2000), pp. 1473–1482; published by American Gastroenterological Association (USA).

Fedorak, R. N. et al., "Human Recombinant Interleukin–10 is Safe and Well Tolerated But Does Not Induce Remission in Steroid Dependent Crohn's Disease," *Gastroenterology,* 120 (Supp. 1) (2001), p. A–127; published by W.B. Saunders (Philadelphia, USA).

Hanauer, S. B. et al., "Evolving Treatment Strategies for Inflammatory Bowel Disease," *Annu. Rev. Med.,* 52 (2001), pp. 299–318; published by Annual Reviews.

Kam, L. Y. et al., "TNF–α antagonists for the treatment of Crohn's disease," *Exp. Opin. Pharmacother.,* 1 (4) (2000), pp. 615–622; published by Ashley Publications Ltd.

Puchner, Thomas C. et al., "Successful Desensitization and Therapeutic Use of Infliximab in Adult and Pediatric Crohn's Disease Patients with Prior Anaphylactic Reaction," *Inflamm. Bowel Dis.,* 7 (1) (2001), pp. 34–37; published by Crohn's & Colitis Foundation of America, Inc. (USA).

Ricart, E. et al., "Infliximab for Crohn's Disease in Clinical Practice at the Mayo Clinic: The First 100 Patients," *Am. J. of Gastroenterology,* 96 (3) (2001), pp. 722–729; published by Am. Coll. of Gasstroenterology (USA).

Sandborn, W. J. et al., "An Engineered Human Antibody to TNF (CDP571) for Active Crohn's Disease: A Randomized Double–Blind Placebo–Controlled Trial," *Gastroenterology,* 120 (2001), pp. 1330–1338; published by American Gastroenterological Association (USA).

Sandborn, W. J. et al., "Etanercept for Active Crohn's Disease: A Randomized, Double–Blind, Placebo–Controlled Trial," *Gastroenterology,* 121 (5) (2001), pp. 1088–1094; published by American Gastroenterological Association (USA).

Sands, B. E. et al., "Infliximab in the Treatment of Severe, Steroid–Refractory Ulcerative Colitis: A Pilot Study," *Inflamm. Bowel Dis.,* 7 (2) (2001), pp. 83–88; published by Crohn's & Colitis Foundation of America, Inc. (USA).

Schreiber, S. et al., "Safety and Efficacy of Recombinant Human Interleukin 10 in Chronic Active Crohn's Disease," *Gastroenterology,* 119 (6) (2000), pp. 1461–1472; published by American Gastroenterological Association (USA).

Schreiber, S. et al., "Immunoregulatory Role of Interleukin 10 in Patients With Inflammatory Bowel Disease," *Gastroenterology,* 108 (5) (1995), pp. 1434–1444; published by American Gastroenterological Association (USA).

Stio, M. et al., "Suppressive effect of 1,25–dihydroxyvitamin $D_3$ and its analogues EB 1089 and KH 1060 on T lymphocyte proliferation in active ulcerative colitis," *Biochemical Pharmacology,* 61 (2001), pp. 365–371; published by Elsevier Science Inc.

Targan, S. R., "Biology of inflammation in Crohn's disease: Mechanisms of action of anti–TNF–α therapy," *Can. J. Gastroenterology,* 14 (Suppl. C) (2000), pp. 13C–16C.

van Berge Henegouwen, G. P., ["Consensus for infliximab treatment of patients with Crohn's disease"], *Ned Tijdschr. Geneeskd.,* 144 (38) (2000), pp. 1844–1845 (Netherlands). English Abstract is provided on p. 1845 of the reference.

van Deventer, S. J. et al., "Multiple Doses of Intravenous Interleukin 10 in Steroid–Refractory Crohn's Disease," *Gastroenterology,* 113 (2) (1997), pp. 383–389; published by American Gastroenterological Association (USA).

Harries, A.D. et al., "Vitamin D status in Crohn's disease: association with nutrition and disease activity," *Gut,* 26 (1985), pp. 1197–1203.

Issenman, R. M., "Bone Mineral Metabolism in Pediatric Inflammatory Bowel Disease," *Inflamm. Bowel Dis.,* 5 (3) (1999), pp. 192–199; published by Crohn's & Colitis Foundation of America, Inc. (USA).

Jahnsen, J. et al., "Vitamin D Status, Parathyroid Hormone and Bone Mineral Density in Patients with Inflammatory Bowel Disease," *Scand. J. Gastroenterol.,* 37 (2002), pp. 192–199; published by Taylor & Francis.

Kirchgatterer, A. et al., "Examination, Prevention and Treatment of Osteoporosis in Patients with Inflammatory Bowel Disease: Recommendations and Reality," *Acta Medica Austriaca,* 29 (2002), pp. 120–123; U.S. Copyright Clearance Center Code Statement; 0303–8173/2002/2904–0120.

Lamb, E. J. et al., "Metabolic bone disease is present at diagnosis in patients with inflammatory bowel disease," *Aliment Pharmacol. Ther.,* 16 (2002), pp. 1895–1902; published by Blackwell Science Ltd.

Scharla, S. H. et al., "Bone mineral density and calcium regulating hormones in patients with inflammatory bowel disease (Crohn's disease and ulcerative colitis)," *Exp. Clin. Endocrinol.,* 102 (1994), pp. 44–49; published by Johann Ambrosius Barth.

Schulte, C. et al., "Reduced Bone Mineral Density and Unbalanced Bone Metabolism in Patients with Inflammatory Bowel Disease," *Inflamm. Bowel Dis.,* 4 (4) (1998), pp. 268–275; published by Crohn's & Colitis Foundation of America, Inc. (USA).

Silvennoinen, J., "Relationships between vitamin D, parathyroid hormone and bone mineral density in inflammatory bowel disease," *J. Intern. Med.,* 239 (2) (1996), pp. 131–137; published by Blackwell Science Ltd.

Sonnenberg, A. et al., "25–Hydroxycholecalciferol Serum Levels in Patients with Crohn's Disease," *Acta Hepato–Gastroenterol.,* 24 (1977), pp. 293–295; published by Georg Thieme Verlag Stuttgart (Germany).

Vogelsang, H. et al., "Bone Disease in Vitamin D–Deficient Patients with Crohn's Disease," *Digestive Diseases and Sciences,* 34 (7) (1989), pp. 1094–1099; published by Plenum Publishing Corporation (USA).

Vogelsang, H. et al., "25–Hydroxyvitamin D. absorption in patients with Crohn's disease and with pancreatic insufficiency," *Wien Klin Wochenschr.,* 109 (17) (1997), pp. 678–682; published by Springer–Verlag (Austria).

MacDermott, R.P., *J. Gastroenterology,* 31:907–916 (1996).*

Boehm et al., *Chemistry & Biology* 6:265–275 (1999).*

Satsangi et al., *Clin. Sci. (Colch),* May;94(5):473–8 (1998).*

Andreassen et al., *Scand. J. Gastroenterol.,* 32:1247–1255 (1997).*

Boot et al., *Gut,* 42:188–94 (1998).*

Duerr et al., *Am. J. Hu. Gen.,* 63:95–100 (1998).*

Labuda et al., *J. Bone Min. Res.* 7:1447–53 (1992.*

Sonnenberg et al., *Gastroenterol.* 102:1827 (1992).*

Shivanada et al., *Gut,* 39:690–7 (1996).*

Moum et al., *Scand. J. Gastroenterol.,* 31:362–6 (1996).*

Radhakrishnan et al., *Digestion,* 58:266–70 (1997).*

Holick, M.F., *Am. J. Clin. Nutr.,* Mar.;61(3 Suppl.):638S–645S (1995).*

Haussler et al., *J. Endocrinol.* 154:557–573 (1997).*

Thomas et al., *N. Eng. J. Med.,* 338:777–783 (1998).*

Fiocchi, C., *Gastroenterology,* 115:182–205 (1998).*

Pallone et al., *Gut,* 28:745–753 (1987).*

Kaulfersch et al., *Gastroenterology,* 95:364–370 (1988).*

Breese et al., *Immunology* 78:127–31 (1993).*

Monteleone et al., *Gastroenterol.,* 112:1169–78 (1997).

Powrie, F., *Immunity,* 3:171–74 (1995).

Sadlack et al., *Cell,* 7:253–61 (1993).

Kuhn et al. *Cell,* 75:63–74 (1993).

Shull et al., *Nature,* 359:693 (1992).

Mombaerts et al., *Cell.* Oct. 22;75(2):274–82 (1993).

Berg et al., *J. Clin. Invest.* 98:1010–20 (1996).

Powrie et al., *J. Exp. Med.* 183:2669–74 (1996).

Cantorna et al., *Proc. Natl. Acad. Sci.* USA, 93:7861–7864 (1996).

Cantorna et al., *J. Nutr.* 128:68–72 (1998).

Cantorna et al., *J. Immunol.* 160:5314–5319 (1998).

Bouillon et al., *Endocr Rev.* Apr.;16(2):200–57 (1995).

Lemire et al., *Endocrinology,* 135:2818–2821, (1994).

Koizumi et al., *Int. Arch. Allergy Appl. Immunol.,* 77:396–404 (1985).

Abe et al., *Endocrinology,* 124:2645–2647 (1989).

Lillevang et al., *Clin. Exp. Immunol.,* 88:301–306 (1992).

Lemire et al., *Transplantation,* 54:762–763 (1992).

Veyron et al., *Transplant Immunol.,* 1:72–76 (1993).

Asou et al., *Blood,* 92:2441–2449 (1998).

Bouillon et al., *J. Biol. Chem.,* 267:3044–3051 (1992).

Norman et al., *Cancer Res.,* 50:6857–6864 (1990).

Perlman et al., *Biochemistry,* 29:190–196.

Okayasu, et al., *Gastro.,* 98:694–702 (1990).

Bradford, M.M., *Anal. Biochem.,* 72:248–254 (1976).

Schefler, W.C., *Statistics for the Biological Sciences,* 2nd Edition, Addison–Wesley Pub. Co., Reading, MA, USA, 1979).

Saitoh, et al., *Digestion* 56:67–75 (1995).

Sugi et al., *Am. J. Gastroenterol.* 91:927 (1996).

Moolenbeek and Ruitenber, *Lab Anim.* 15:57–59 (1981).

Boehm et al., Chemistry & Biology 6:265–275 (1999).

Mahler et al., *Am. J. Physiol.—Gastro. & Liver Physiol.,* 37 G: 544–G 551, (1998).

Hogaboam et al., *J. Clin. Invest.,* 100:2766–76 (1997).

Krawisz et al., *Gastroenterol.* 87:1344–50 (1984).

Schneider and Issekutz, *J. Immunol. Methods,* 198:1–14 (1996).

Dwarakanath et al., *Clin. Sci.* 92:307–13 (1997).

Chan et al., *Cur. Prob. Surgery,* 34:445–523 (1997). At the present time we are unable to obtain a copy of this reference. If the Examiner needs this reference please contact our offices and we will obtain a copy.

Strober et al., *Immunol. Today,* Feb.;18(2):61–4 (1997).

Caccavo et al., *Hybridoma* 15:263–269 (1996).

Best et al., *Gastroenterology* 70:439–444 (1976).

Bregenholt et al., *Eur. J. Immunol.* 28:379–389 (1998).

Groux et al., *Nature* 389:737–742 (19997).

Romagnani et al., *Cur. Opin. in Immunology* 9:793–799 (1997).

Cong et al., *J. Exp. Med.* 187:855–864 (1998).

Davidson et al., *J. Exp. Med.* 184:241–251 (1996).

Hugot et al., *Nature* 379:821–823 (1996).

Satsangi et al., *Nature Genetics* 14:199–202 (1996).

Sonnenberg et al., *Gastroenterology* 101:122–130 (1991).

Robinson, *Amer. J. of Gastro.* 92:12S–17S (1997).

Kornbluth et al., *Amer. J. of Gastro.* 92:1424–1248 (1997).

Targan et al., *New England Journal of Medicine* 337:1029–1035 (1997).

Elson et al., *Gastroenterology* 109:1344–1367 (1995).

Strober et al., *Cell* 75:203–205 (1993).

Targen et al., *Nature Medicien* 1:1241–1243 (1995).

Sartor, *AJG* 92:5S–11S (1997).

Sonnenberg et al., *Gastro.* 100:143–149 (1991).

Danze et al., *Gut* 39:69–72 (1996).

Schneider et al., *J. of Immun. Methods* 198:1–14 (1996).

King et al., *J. of Leukocyte Biology* 61:293–302 (1997).

Motley et al., *bone and Mineral* 23:95–104 (1993).

Bouillon et al., *Horm Res.* 45:117–121 (1996).

Binderup *Biochemical Pharmacology* 43:1885–1892 (1992).

Ostrem et al., *Proc. Natl. Acad. Sci. USA* 84:2610–2614 (1987).
Sellon et al., *Infect. and Immun.,* 66:5224–5231 (1998).
Cantorna et al., *J. Nutr.,* 129(11):1966–71 (1999).
Cantorna et al., 66:828–831 (1998).
Bhan et al., *Immunol. Reviews,* 169:195–207 (1999).
Fort et al., *J. Immunol.,* 161:3256–61 (1998).
Davidson et al. *J. Immunol.,* 161:3143–9 (1998).
Sandler et al., *Inflamm. Bowel Dis.,* 4:175–6 (1998).

DeLuca, Hector et al., "Vitamin D: Its Role and Uses in Immunology," *The FASEB Journal*, 2001, vol. 15, pp. 2579–2585.

Breese, E. et al., "Interleukin–2–and interferon–gamma–secreting T cells in normal and diseased human intestinal mucosa," *Immunology*, 1993, vol. 78, pp. 127–131.

* cited by examiner-

LG190090

LG190119

LG190155

LG190176

LG190178

USE OF BIOLOGICALLY ACTIVE VITAMIN D COMPOUNDS FOR THE PREVENTION AND TREATMENT OF INFLAMMATORY BOWEL DISEASE

The present Application is a Continuation of application Ser. No. 09/469,985, filed Dec. 21, 1999, which is now U.S. Pat. No. 6,358,939.

FIELD OF THE INVENTION

The present invention relates to therapeutics for the prevention and treatment of inflammatory bowel disease, and in particular the prevention and treatment of inflammatory bowel disease in humans as well as other animals through the use of biologically active vitamin D compounds.

BACKGROUND OF THE INVENTION

Inflammatory bowel diseases (IBD) are defined by chronic, relapsing intestinal inflammation of obscure origin. IBD refers to two distinct disorders, Crohn's disease and ulcerative colitis (UC). Both diseases appear to involve either a dysregulated immune response to GI tract antigens, a mucosal barrier breach, and/or an adverse inflammatory reaction to a persistent intestinal infection. The GI tract luminal contents and bacteria constantly stimulate the mucosal immune system, and a delicate balance of proinflammatory and anti-inflammatory cells and molecules maintains the integrity of the GI tract, without eliciting severe and damaging inflammation [MacDermott, R. P., *J. Gastroenterology*, 31:907:–916 (1996)]. It is unknown how the IBD inflammatory cascade begins, but constant GI antigen-dependent stimulation of the mucosal and systemic immune systems perpetuates the inflammatory cascade and drives lesion formation.

There is no known cure for IBD, which afflicts 2 million Americans. Current methods of managing IBD symptoms cost an estimated $1.2 billion annually in the United States alone.

In patients with IBD, ulcers and inflammation of the inner lining of the intestines lead to symptoms of abdominal pain, diarrhea, and rectal bleeding. Ulcerative colitis occurs in the large intestine, while in Crohn's, the disease can involve the entire GI tract as well as the small and large intestines. For most patients, IBD is a chronic condition with symptoms lasting for months to years. It is most common in young adults, but can occur at any age. It is found worldwide, but is most common in industrialized countries such as the United States, England, and northern Europe. It is especially common in people of Jewish descent and has racial differences in incidence as well. The clinical symptoms of IBD are intermittent rectal bleeding, crampy abdominal pain, weight loss and diarrhea. Diagnosis of IBD is based on the clinical symptoms, the use of a barium enema, but direct visualization (sigmoidoscopy or colonoscopy) is the most accurate test. Protracted IBD is a risk factor for colon cancer. The risk for cancer begins to rise significantly after eight to ten years of IBD.

Some patients with UC only have disease in the rectum (proctitis). Others with UC have disease limited to the rectum and the adjacent left colon (proctosigmoiditis). Yet others have UC of the entire colon (universal IBD). Symptoms of UC are generally more severe with more extensive disease (larger portion of the colon involved with disease).

The prognosis for patients with disease limited to the rectum (proctitis) or UC limited to the end of the left colon (proctosigmoiditis) is better then that of full colon UC. Brief periodic treatments using oral medications or enemas may be sufficient. In those with more extensive disease, blood loss from the inflamed intestines can lead to anemia, and may require treatment with iron supplements or even blood transfusions. Rarely, the colon can acutely dilate to a large size when the inflammation becomes very severe. This condition is called toxic megacolon. Patients with toxic megacolon are extremely ill with fever, abdominal pain and distention, dehydration, and malnutrition. Unless the patient improves rapidly with medication, surgery is usually necessary to prevent colon rupture.

Crohn's disease can occur in all regions of the gastrointestinal tract. With this disease intestinal obstruction due to inflammation and fibrosis occurs in a large number of patients. Granulomas and fistula formation are frequent complications of Crohn's disease. Disease progression consequences include intravenous feeding, surgery and colostomy.

The most commonly used medications to treat IBD are anti-inflammatory drugs such as the salicylates. The salicylate preparations have been effective in treating mild to moderate disease. They can also decrease the frequency of disease flares when the medications are taken on a prolonged basis. Examples of salicylates include sulfasalazine, olsalazine, and mesalamine. All of these medications are given orally in high doses for maximal therapeutic benefit. These medicines are not without side effects. Azulfidine can cause upset stomach when taken in high doses, and rare cases of mild kidney inflammation have been reported with some salicylate preparations.

Corticosteroids are more potent and faster-acting than salicylates in the treatment of IBD, but potentially serious side effects limit the use of corticosteroids to patients with more severe disease. Side effects of corticosteroids usually occur with long term use. They include thinning of the bone and skin, infections, diabetes, muscle wasting, rounding of faces, psychiatric disturbances, and, on rare occasions, destruction of hip joints.

In IBD patients that do not respond to salicylates or corticosteroids, medications that suppress the immune system are used. Examples of immunosuppressants include azathioprine and 6-mercaptopurine. Immunosuppressants used in this situation help to control IBD and allow gradual reduction or elimination of corticosteroids. However, immunosuppressants cause increased risk of infection, renal insufficiency, and the need for hospitalization.

Clearly there is a great need for agents capable of preventing and treating IBD. It would be desirable if such agents could be administered in a cost-effective and timely fashion, with a minimum of adverse side effects.

Definitions

The phrase "vitamin D compounds" include, but are not limited to compounds which have at least one of the following features: the C-ring, D-ring and 3β-hydroxycyclohexane A-ring of vitamin D interconnected by the 5,7 diene double bond system of vitamin D together with any side chain attached to the D-ring (i.e. compounds with a 'vitamin D nucleus' and substituted or unsubstituted A-, C-, and D-rings interconnected by a 5,7 diene double bond system typical of vitamin D together with a side chain attached to the D-ring).

The phrase "nonsecosteroidal vitamin D mimics" is defined as nonsecosteroid compounds which are capable of mimicking various activities of the secosteroid calcitriol. Examples of such compounds include, but are not limited to, LG190090, LG190119, LG190155, LG190176, and LG1900178 [See, Boehm et al., *Chemistry & Biology* 6:265–275 (1999)].

The phrase "biologically active vitamin D compound" is defined as encompassing vitamin D compounds and non-secosteroidal vitamin D mimics which are biologically active in vivo, or are acted upon in a subject (i.e. host) such that the compound becomes active in vivo. Examples of such compounds include, but are not limited to: vitamin D, 1,25 dihydroxyvitamin $D_3$ (1,25$(OH)_2D_3$) [a.k.a. calcitriol], and analogs thereof [e.g. 1α-hydroxyvitamin $D_3$ (1α-OH-$D_3$), 1,25-dihydroxyvitamin $D_2$ (1,25-$(OH)_2D_2$), 1α-hydroxyvitamin $D_2$ (1α-OH-$D_2$), 1α,25-$(OH)_2$-16-ene-$D_3$, 1α,25-$(OH)_2$-24-oxo-16-ene-$D_3$, 1α,24R$(OH)_2$-$D_3$, 1α,25$(OH)_{2-22}$-oxa-$D_3$, 20-epi-22-oxa-24a,24b,-dihomo-1α,25$(OH)_2$-$D_3$, $_{20}$-epi-22-oxa-24a,26a,27a,-trihomo-1α,25$(OH)_2$-$D_3$, 20-epi-22-oxa-24homo-1α,25$(OH)_2$-$D_3$, 1,25-$(OH)_2$-16,23E-diene-26-trifluoro-19-nor-$D_3$, and nonsecosteroidal vitamin D mimics. Further examples are provided below, including various structural formulas, detailed in part III.

The phrase "symptoms of IBD" is herein defined to include symptoms, including, but not limited to, abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding).

The phrase "calcemic response" is herein defined as the biological response caused by many biologically active vitamin D compounds (e.g. calcitriol) when administered to a subject. The response includes, but is not limited to, elevated calcium concentrations in serum, increased intestinal absorption of dietary calcium, increased urinary calcium excretion, and increased bone calcium mobilization.

The phrase "symptoms of hypercalcemia" is herein defined to detected symptoms including, but not limited to, calcium deposition in the kidneys (nephrocalcinosis), kidney stones (nephrolithiasis), uremia, manifestations of muscle weakness, lethargy, coma, constipation, anorexia, nausea, vomiting, shortening of the QT interval, hypotension, and arrhythmias.

The phrase "serious hypercalcemia" is herein defined as the condition where a subject is suffering from symptoms of hypercalcemia which require immediate medical attention to prevent life threatening illness or death. Examples include, but are not limited to, nephrocalcinosis, nephrolithiasis, uremia, coma, and anorexia.

The phrase "mild hypercalcemia" is herein defined as the condition where a subject is suffering from symptoms of hypercalcemia which do not require immediate medical attention to prevent life threatening illness or death. Examples include, but are not limited to, manifestations of muscle weakness, lethargy, constipation, nausea, vomiting, shortening of the QT interval, hypotension, and arrhythmia.

The phrase "a therapeutically effective amount" of a biologically active vitamin D compound is herein defined as the dosage level required for a patient such that the symptoms of IBD are reduced.

The phrase "under conditions such that the symptoms are reduced" refers to any degree of qualitative or quantitative reduction in detectable symptoms of IBD, including but not limited to, a detectable impact on the rate of recovery from disease (e.g. rate of weight gain), or the reduction of at least one of the following symptoms: abdominal pain, diarrhea, rectal bleeding, weight loss, fever, loss of appetite, dehydration, anemia, distention, fibrosis, inflamed intestines and malnutrition.

The phrase "at risk for IBD" is herein defined as encompassing the segment of the world population that has an increased risk (i.e. over the average person) for IBD. IBD is most commonly found in young adults, but can occur at any age. It occurs worldwide, but is most common in the United States, England, and northern Europe. It is especially common in people of Jewish descent. An increased frequency of this condition has been recently observed in developing nations. Increased risk is also present in people with family members who suffer from inflammatory bowel disease.

The phrase "therapeutic composition comprising biologically active vitamin D compounds" refers to compositions containing the biologically active vitamin D compounds of the present invention, or the biologically active vitamin D compounds of the present invention provided together with one or more other compounds or agents including, but not limited to, other biologically active vitamin D compounds, physiologically tolerable liquids, gels, carriers, diluents, adjuvants, excipients, salicylates, steroids, immunosuppressants, antibodies, cytokines, antibiotics, binders, fillers, preservatives, stabilizing agents, emulsifiers, and buffers.

The phrase "continuous manner" when used in reference to the method of delivery or administration of the biologically active vitamin D compounds of the present invention, is defined as meaning a substantially uninterrupted administration of the compounds of the present invention, such that a therapeutic dosage is stretched over a period of time and avoids a dosage 'spike' which is common among other modes of administration (e.g. oral administration or intravenous administration). Examples of modes of administration which employ a continuous manner of delivery include, but are not limited to, a transdermal patch, a suppository, or a slow release oral formulation.

The word "subject" refers to a patient which is administered the therapeutic composition comprising biologically active vitamin D compounds of the present invention. Examples of subjects, include, but are not limited to, humans and other animals such as non-human primates, horses, dogs, and cats.

SUMMARY OF THE INVENTION

The present invention relates to therapeutics for the prevention and treatment of IBD. Specifically, the present invention contemplates the prevention and treatment of IBD in humans as well as other animals through the use of biologically active vitamin D compounds.

The present invention provides a method of treatment, comprising; providing a subject and a therapeutic composition comprising a biologically active vitamin D compound; and administering the therapeutic composition to the subject. It is not intended that the present invention be limited to any particular subject. Indeed, a variety of subjects are contemplated. In one embodiment, the subject is a mammal. In a further embodiment, the subject is a mammal selected from the group of a human, horse, non-human primate, dog, and cat. In a preferred embodiment, the subject is a human. In an additional embodiment, the subject is on a low calcium diet.

In one embodiment, the subject is suffering from symptoms of inflammatory bowel disease. In another embodiment, the subject is suffering from ulcerative colitis. In a different embodiment, the subject is suffering from Crohn's disease. In a preferred embodiment, the administration of a therapeutic composition comprising a biologically active vitamin D compound reduces the symptoms of disease (i.e. reduces the symptoms of inflammatory bowel disease, ulcerative colitis, or Crohn's disease). In another embodiment, the biologically active vitamin D compounds are administered under conditions such that the symptoms of IBD are reduced. In a different embodiment, the subject is at risk for inflammatory bowel disease, and the therapeutic composition is administered prophylactically. In still further embodiments, a therapeutically effective amount of a biologically active vitamin D compound is administered to the subject.

It is not intended that the present invention be limited to particular biologically active vitamin D compounds. A variety of biologically active vitamin D compounds are contemplated. In one embodiment, the biologically active vitamin D compound is selected from vitamin D, 1,25 dihydroxyvitamin $D_3$, 1α-hydroxyvitamin $D_3$, 1,25-dihydroxyvitamin $D_2$, $_1$α-hydroxyvitamin $D_2$, 1α,25-(OH)$_2$-16-ene-$D_3$, 1α,25-(OH)$_2$-24-oxo-16-ene-$D_3$, 1α,24R(OH)$_2$-$D_3$, 1α,25(OH)$_2$-22-oxa-$D_3$, 20-epi-22-oxa-24a,24b,-dihomo-1α,25(OH)$_2$-$D_3$, 20-epi-22-oxa-24a,26a, 27a,-trihomo-1α,25(OH)$_2$-$D_3$, 20-epi-22-oxa-24homo-1α, 25(OH)$_2$-$D_3$, 1,25-(OH)$_2$-16,23E-diene-26-trifluoro-19-nor-$D_3$. In a preferred embodiment, the biologically active vitamin D compound is selected from 1,25-dihydroxyvitamin $D_3$, 19-nor-1,25-dihydroxyvitamin $D_2$, 19-nor-1,25-dihydroxy-21-epi-vitamin $D_3$, 1,25-dihydroxy-24-homo-22-dehydro-22E-vitamin $D_3$, and 19-nor-1,25-dihydroxy-24-homo-22-dehydro-22E-vitamin $D_3$, and non-secosteroidal vitamin D mimics. In a particularly preferred embodiment, the biologically active compound is 1,25-dihydroxyvitamin $D_3$. In an additional embodiment, the biologically active vitamin D compound is selected from the analogs represented by the following formula:

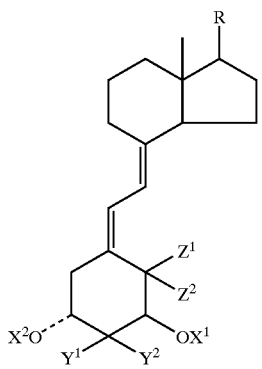

wherein $X^1$ and $X^1$ are each selected from the group consisting of hydrogen and acyl;

wherein $Y^1$ and $Y^2$ can be H, or one can be O-aryl or O-alkyl while the other is hydrogen and can have a β or α configuration, $Z^1$ and $Z^2$ are both H, or $Z^1$ and $Z^2$ taken together are CH$_2$; and wherein R is an alkyl, hydroxyalkyl or fluoroalkyl group, or R may represent the following side chain:

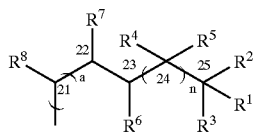

wherein (a) may have an S or R configuration and wherein $R^1$ represents hydrogen, hydroxy or O-acyl, $R^2$ and $R^3$ are each selected from the group consisting of alkyl, hydroxyalkyl and fluoroalkyl, or, when taken together represent the group —(CH$_2$)m— where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, hydroxy, fluorine, alkyl, hydroxyalkyl and fluoroalkyl, or, $R^4$ and $R^5$ taken together represent double-bonded oxygen, $R^6$ and $R^7$ taken together form a carbon-carbon double bond and $R^8$ may be H or CH$_3$, and wherein n is an integer having a value of from 1 to 5, and wherein the carbon at any one of positions 20, 22, or 23 in the side chain may be replaced by an O, S, or N atom.

In one embodiment, the biologically active vitamin D compounds of the present invention do not cause symptoms of hypercalcemia when administered to a subject. In another preferred embodiment of the present invention, the biologically active vitamin D compounds of the present invention do not generate as much (i.e. a lesser degree) of a calcemic response as compared to calcitriol when administered to a subject. In one embodiment, the biologically active vitamin D compounds have low calcemic response characteristics, inhibit cell proliferation and promote cell differentiation as compared to calcitriol. In another embodiment, these compounds are selected from 1α,25-(OH)$_2$-24-epi-$D_2$, α,25-(OH)$_2$-24a-Homo-$D_3$, 1α,25-(OH)$_2$-24a-Dihomo-$D_3$, 1α,25-(OH)$_2$-19-nor-$D_3$, and 20-epi-24-homo-1α,25-(OH)$_2$-$D_3$.

The present invention also contemplates the administration of a therapeutic composition comprising more than one of the biologically active compounds of the present invention. In other embodiments, the biologically active compounds of the present invention are administered in therapeutically effective amounts. In one embodiment, a preferred dose of the biologically active vitamin D compound for the present invention is the maximum that a patient can tolerate and not develop serious hypercalcemia. In another embodiment, if the biologically active vitamin D compound is not a 1α-hydroxy compound, a daily dose between 1.0 and 100 μg per day per 160 pound patient is administered, while a particularly advantageous daily dose is between 5.0 and 50 μg per day per 160 pound patient. In a different embodiment, if the biologically active vitamin D compound is a 1α-hydroxy compound, a daily dose of between 0.1 and 20 μg per day per 160 pound patient is administered, while a preferred dose is between 0.5 and 10 μg per day per 160 pound patient. In a particularly preferred embodiment, the dose is between 3–10 μg per day. In an additional embodiment, the therapeutic administration of the biologically active vitamin D compounds does not cause serious hypercalcemia. In another embodiment, the therapeutic administration of the biologically active vitamin D compounds only causes mild hypercalcemia. In another embodiment, the biologically active vitamin D compounds do not cause symptoms of hypercalcemia.

It is not intended that the present invention be limited to a particular mode of administration. A variety of modes of administration are contemplated, including intravenously, intramuscularly, subcutaneously, intradermally, intraperitoneally, intrapleurally, intrathecally, orally, rectally and topically. In certain embodiments, the therapeutic compositions are administered via suppository, or in tablet or capsule formulations for oral delivery. In one embodiment, administration of the therapeutic compositions occurs at night. In another embodiment, multiple doses (e.g. 3 or 4) are provided in a 24 hour period. In a further embodiment, the administration of the therapeutic composition is by pulse intravenous therapy. In a particularly preferred embodiment, the therapeutic compositions are administered via a transdermal patch (skin patch).

The present invention also provides a method of treatment, comprising, providing a subject with symptoms of inflammatory bowel disease and a therapeutic composition comprising a biologically active vitamin D compound, and administering the therapeutic compound to the subject. In one embodiment, the biologically active vitamin D compounds are administered to a patient after the surgical removal of damaged tissue. In a preferred embodiment, the present invention provides a method of treatment, comprising, providing a human patient with symptoms of inflammatory bowel disease, a therapeutic composition comprising a biologically active vitamin D compound, and administering the therapeutic composition to the patient under conditions such that said symptoms are reduced.

The present invention also provides a method of treatment, comprising, providing a subject at risk for inflammatory bowel disease and a therapeutic composition comprising a biologically active vitamin D compound, and prophylactically administering the therapeutic compound to the subject. In a preferred embodiment, the prophylactic administration of the biologically active vitamin D compounds delays the onset of the symptoms of inflammatory bowel disease. In a particularly preferred embodiment, the prophylactic administration of the biologically active vitamin D compounds prevents the onset of one or more symptoms of inflammatory bowel disease (e.g. prevents the onset of abdominal pain, diarrhea, rectal bleeding, weight loss, fever, loss of appetite, dehydration, anemia, or malnutrition, or any combination thereof).

The present invention also provides a composition of matter comprising a transdermal patch, wherein said transdermal patch comprises a therapeutic composition comprising biologically active vitamin D compounds. In one embodiment, the transdermal patch comprises a therapeutically effective amount of a biologically active vitamin D compound. In another embodiment, the transdermal patch further comprises a single polymer. In an additional embodiment, the transdermal patch further comprises multiple polymers. In another embodiment, the transdermal patch further comprises a polyurethane acrylic copolymer. In another embodiment, the transdermal patch further comprises silicone or polyisobutylene or both. In a preferred embodiment, the transdermal patch is worn by a subject at risk for Inflammatory Bowel Disease. In another preferred embodiment, the transdermal patch is worn by a subject with symptoms of Inflammatory Bowel Disease. In another embodiment, the transdermal patch delivers biologically active vitamin D compounds to a subject in a continuous manner under conditions such that symptoms of IBD are reduced.

DESCRIPTION OF THE INVENTION

Figure 1:
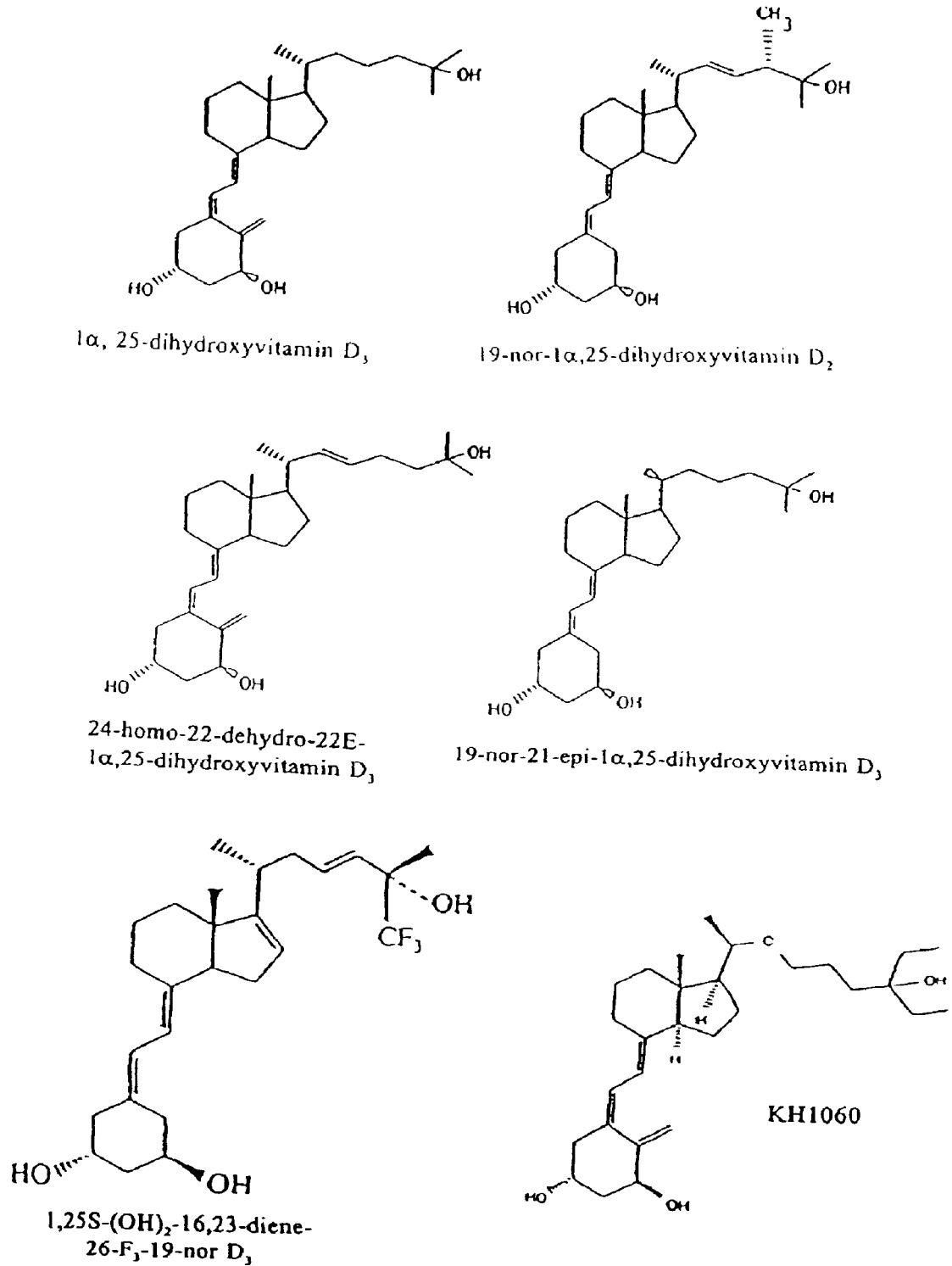
FIG. 1 depicts six biologically active vitamin D compounds useful in the present invention.
Figure 2:
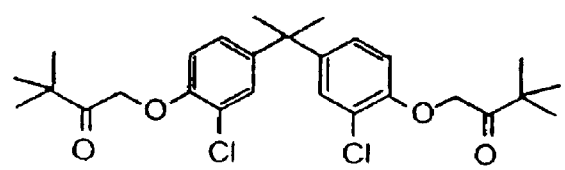
FIG. 2 depicts five nonsecosteroidal vitamin D compounds (mimics) useful in the present invention.
Figure 2:
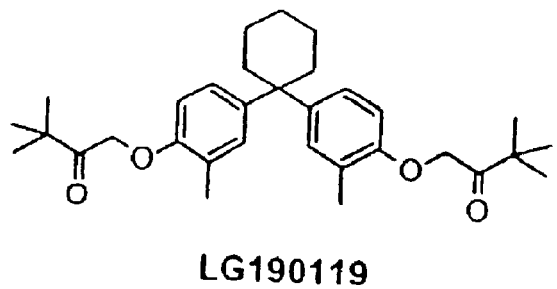
Figure 2:
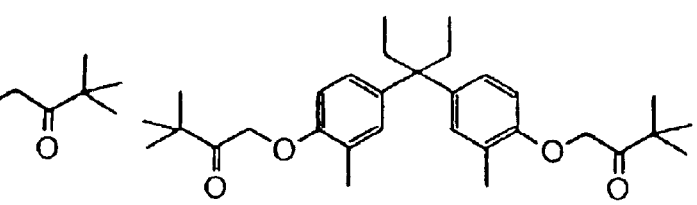
Figure 2:
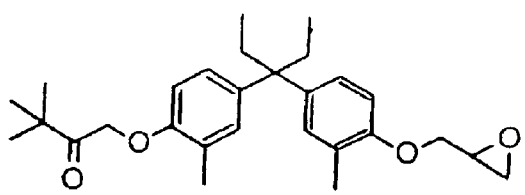
Figure 2:
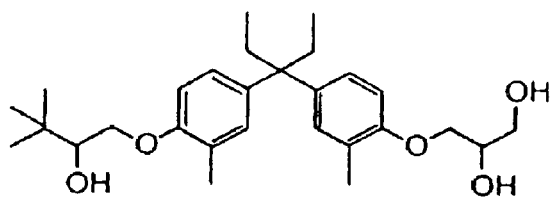

The present invention relates to therapeutic compositions and methods for the prevention treatment of IBD, and in particular the prevention and treatment of IBD in humans as well as other animals through the use of biologically active vitamin D compounds.

I. Intestinal Bowel Disease Risk Factors and Vitamin D

Intestinal Bowel Disease (IBD) encompasses both Crohn's Disease (CD) and Ulcerative Colitis (UC). CD and UC are distinct, but related polygenic disorders. Familial clustering of IBD strongly suggests that IBD susceptibility genes contribute to disease development. The relative risk of IBD among siblings of CD patients was 36.5 and among siblings of UC patients was 16.6, compared to the general population. Possible IBD susceptibility genes have been mapped to chromosomes 2, 3, 6, 7, 12 and 16. The identity and function of these susceptibility genes is unknown [See, Satangi et al., *Clin. Sci.* (*Colch*), May;94(5):473–8 (1998)].

Vitamin D stimulates bone mineralization, and there is evidence for poor bone mineralization in IBD patients [Andreassen et al., *Scand. J. Gastroenterol.*, 32:1247-1255 (1997)]. Many reports found osteoporosis in greater than 40% of adult CD patients, while pediatric CD patients had significantly decreased bone length and mineral density compared to controls [Boot et al., *Gut*, 42:188–94 (1998)]. Neither malabsorption, nor steroid use explained the poor bone mineralization. Recently, an IBD susceptibility locus was mapped to chromosome 12 [Satangi et al., *Clin. Sci.* (*Colch*), May;94(5):473–8 (1998), and Duerr et al., *Am. J. Hu. Gen.*, 63:95–100 (1998)]. This IBD susceptibility locus is in the same region as the vitamin D receptor and the 25-hydroxyvitamin $D_3$-1-α-hydroxylase genes [Labuda et al., *J. Bone Min. Res.* 7:1447–53 (1992)].

It is not intended that the present invention be limited to a particular mechanism of action. Indeed, an understanding of the mechanism is not necessary to make and use the present invention. However, it is believed that there may be a genetic defect in calcitriol synthesis, transport, or utilization which underlies a dual phenotype of decreased bone mineralization and susceptibility to IBD in some individuals. As such, the therapeutic affect of the administration of biologically active vitamin D compounds to patients may be achieved (at least in part) by compensating for these genetic defects.

Inheriting IBD susceptibility genes, however, is not sufficient for disease development. Environmental risk factors may be of equal or greater significance in determining IBD. IBD prevalence studies show a striking latitude gradient in the United States [Sonnenber et al., *Gastroenterol.* 102:1827 (1992)], and Europe [Shivananda et al., *Gut*, 39:690–7 (1996)]. The IBD incidence is high at northern latitudes and low at southern latitudes. For Example, there are 21 UC patients per 100,000 population aged 25–34 years in Norway [Moum et al., *Scand. J. Gastroenterol.*, 31:362–6 (1996)], but only 1 UC patient per 100,000 population in Oman [Radhakrishnan et al., *Digestion*, 58:266–70 (1997)]. Therefore, while the IBD-determining environmental risk factor has not been identified yet, it appears to correlate strongly with latitude.

Vertebrates, including humans, obtain the majority of the daily requirement of vitamin D from casual exposure to sunlight [Holick, M. F., *Am. J. Clin. Nutr.*, Mar;61(3 Suppl.):638S-645S (1995)]. UV light from the sun (282–310 nm) catalyzes a chemical photolysis reaction in the skin, converting 7-dehydrocholesterol to previtamin $D_3$, which spontaneously isomerizes to vitamin $D_3$ [Holick, M. F., *Bone*, 7:66–69 (1990)]. Vitamin $D_3$ is biologically inert, and must be activated by 25-hydroxylation in the liver and 1α-hydroxylation in the kidney to produce the vitamin D hormone 1α,25-dihyroxyvitamin $D_3$ (calcitriol) [Haussler et al., *J. Endocrinol.* 154:557–573 (1997)]. Above 52°N, there is insufficient sunlight intensity to catalyze vitamin D biosynthesis from October to April, whereas vitamin D biosynthesis occurs year-round below 34°N [Holick, M. F., *Am. J. Clin. Nutr.*, March;61(3 Suppl.):638S-645S (1995)]. Vitamin D deficiency is common at northern latitudes. In one study, at 42°N, vitamin D deficiency affected 57% of a random population sample [Thomas et al., *N. Eng. J. Med.*, 338:777–783 (1998)].

It is not intended that the present invention be limited to a particular mechanism of action. Indeed, an understanding of the mechanism is not necessary to make and use the present invention. However, it is believed that insufficient sunlight for vitamin $D_3$ biosynthesis may be a disease-determining environmental risk factor for IBD. As such, the therapeutic affect of the administration of biologically active vitamin D compounds to patients may be achieved by compensating for insufficient vitamin D biosynthesis in certain patients.

There is evidence that immune responses to GI tract microbes are involved in IBD pathology, but no specific microbe or microbial antigen has been implicated in IBD etiology [Fiocchi, C., *Gastroenterology*, 115:182–205 (1998)]. Antibodies and cells reactive with autoantigens have been detected, but their relevance to disease etiology is debated. T lymphocyte infiltration of the mucosa is characteristic of IBD; these infiltrating cells display activation markers [Pallone et al., *Gut*, 28:745–753 (1987], and broad specificity [Kaulfersch et al., *Gastroenterology*, 95:364–370 (1988)]. In CD, mucosal T cells display upregulated IL-2 receptors, and spontaneously produce IL-2 and IFN-γ [Breese et al., *Immunology*, 78:127–31 (1993)]. Moreover, CD mucosal cells spontaneously secrete IL-12 [Monteleone et al., *Gastroenterol.*, 112:1169–78 (1997)]. These observations, together with the consistent finding of upregulated proinflammatory cytokines in IBD mucosa [Fiocchi, C., *Gastroenterology*, 115:182–205 (1998)], has suggested the hypothesis that IBD represents a dysregulated, T helper type 1 (Th1) driven immune response to the constant antigenic stimulation in the gut, with tissue damage being attributable to inflammatory mediators [Powrie, F., *Immunity*, 3:171–74 (1995)]. The opposing anti-inflammatory responses that maintain tolerance to enteric antigens appear to be dysfunctional in IBD.

Knockout animal models in the cytokine genes IL-2 [Sadlack et al., *Cell*, 75:253–61 (1993)], IL-10 [Kuhn et al. *Cell*, 75:63–74 (1993)], and TGF-β1 [Shull et al., *Nature*, 359:693 (1992)] all spontaneously develop a chronic IBD that shares histopathological features with human IBD. The T cell receptor (TCR) α mutant, TCR β mutant, and class II major histocompatibility complex (MHC) mutant mice also develop spontaneous IBD [Mombaerts et al., *Cell*. Oct. 22;75(2):274–82 (1993)]. In these and other animal models of IBD, Th1 cells have been implicated in disease pathology [Berg et al., *J. Clin. Invest.* 98:1010–20 (1996)], while cells producing TGF-β have a particularly important regulatory role as suppressors of unchecked, Th1-driven inflammatory colitis [Powrie et al., *J. Exp. Med.* 183:2669–74 (1996)].

It has been shown that calcitriol is a potent and selective inhibitor of autoimmune disease in mice. For example, calcitriol administered to mice blocked disease induction for EAE [Cantorna et al., *Proc. Natl. Acad. Sci. USA*, 93:7861–7864 (1996)], Lyme arthritis and collagen induced arthritis [Cantoma et al., *J. Nutr.* 128:68–72 (1998)]. Furthermore, administering calcitriol to animals before EAE induction, or to animals with stage 1 EAE, arrested the clonal expansion of Th1 cells producing IFN-γ and TNF-α, and stimulated an increase in transcript accumulation for anti-inflammatory cytokines TGF-β1 and IL-4, in the central nervous system and lymph nodes [Cantorna et al., *J. Immunol.* 160:5314–5319 (1998)]. It has been shown that cells producing TGF-β1 have a crucial regulatory role as opponents of unchecked, Th-1 driven inflammatory responses [Shull et al., *Nature* 359:693 (1992), and Powrie et al., *J. Exp. Med.* 183:2669–74 (1996)].

It is not intended that the present invention be limited to a particular mechanism of action. Indeed, an understanding of the mechanism is not necessary to make and use the present invention. However, it is believed that the administration of calcitriol increases TGF-β1 expression, thus stimulating a therapeutic anti-inflammatory response in subjects with inflammatory bowel diseases.

II. Treatment of IBD With Biologically Active Vitamin D Compounds

The present invention contemplates the prevention and treatment of Inflammatory Bowel Disease in a subject through the use of biologically active vitamin D compounds. Various forms of treatment and dosages are contemplated, as well as the avoidance of the development of the symptoms of hypercalcemia.

A. Treatment and Dosage

The present invention contemplates both the treatment and prevention of IBD in humans as well as other animals (e.g. mammals) with biologically active vitamin D compounds in therapeutic amounts. It is not intended that the present invention be limited to particular dosages. A broad range of dosages for the therapeutic administration of the biologically active vitamin D compounds are contemplated. In one embodiment, a preferred dose of the biologically active vitamin D compound for the present invention is the maximum that a patient can tolerate and not develop serious hypercalcemia. If the biologically active vitamin D compound is not a 1a-hydroxy compound, a daily dose between 1.0 and 100 μg per day per 160 pound patient is administered, while a particularly advantageous daily dose is between 5.0 and 50 μg per day per 160 pound patient. If the biologically active vitamin D compound is a 1α-hydroxy compound, a daily dose of between 0.1 and 20 μg per day per 160 patient is administered, while a preferred dose is between 0.5 and 10 μg per day per 160 pound patient. In a particularly preferred embodiment, the dose is between 3–10 μg per day. In general, a preferred dose is the highest amount of the biologically active vitamin D compound the patient can tolerate. The dose is preferably divided between two, three, four or five treatments within a 24 hour period.

In the United States, the accepted safe dose of 1,25($OH_2$) $D_3$ and 19-nor-21-epi-1,25($OH_2$)$D_3$ in patients having normal calcium intakes is between 0.5 and 15 μg per day for 1,25($OH_2$)$D_3$, and is 10–20 μg/day for 19-nor-1,25-($OH)_2D_2$. Therefore, a preferred dose for patients with normal calcium intakes is between 0.5 and 0.75 μg per day for a 160 pound patient depending on the compound administered. Patients on a low calcium diet, and/or if the compounds are administered at night, may tolerate more per day (e.g., 3 μg more per day). Therefore, in one embodiment of the present invention, treatment with biologically active vitamin D compounds is administered in as high a dose as the patient can tolerate without developing symptoms of hypercalcemia. In this regard, high doses (e.g. 3–10 μg per day) are administered. However, for 19-nor-1,25($OH_2$)$D_2$ and 24-homo-22-dehydro-22E-1α,25($OH_2$)$D_3$ the safe dosage range is 10–20 μg per day per 160 pound patient.

A determination of whether a patient is benefiting from treatment (i.e. wherein symptoms are reduced), is performed by monitoring the qualitative and quantitative symptoms of IBD. Qualitative symptoms which may monitored include, but are not limited to, abdominal pain, diarrhea, rectal bleeding, weight loss, fever, loss of appetite, dehydration, anemia, and malnutrition. Quantitative symptoms which may be monitored include, but are not limited to, weight loss, fever, and anemia (using a blood test). A successful treatment is indicated wherein the symptoms of IBD are reduced. Preferably, treatment should continue as long as IBD symptoms are suspected or observed.

A determination of whether a subject would benefit from prophylactic treatment of IBD is determined by assessing various risk factors. In other words, a determination of whether a subject is at risk for IBD is made. It is not intended that the present invention be limited to particular risk factors. Indeed, a variety of risk factors may be monitored, including, but not limited to; genetic predisposition, amount of sunlight the patient normally receives, the age of the patient (common in young people), nationality (common in U.S, England, and Northern Europe), and ancestry/race (common in people of Jewish decent). Patients at risk are prophylactically administered the therapeutic compositions of the present invention to delay or prevent the onset of symptoms of IBD.

B. Hypercalcemia

As mentioned above, a preferred dose of vitamin D compound for the present invention is the maximum that a patient can tolerate and not develop serious hypercalcemia. Hypercalcemia is a risk in the administration of biologically active vitamin D compounds (e.g. calcitriol) because the major physiological function of vitamin D is to maintain extracellular calcium levels within a very limited normal range for normal cellular and metabolic processes (including neuromuscular function and bone mineralization). To maintain serum calcium levels, calcitriol primarily increases intestinal absorption of dietary calcium and phosphate, and when required, mobilizes bone calcium. Thus, calcitriol has a potent calcemic effect (i.e. generates a calcemic response in a subject). Therefore, the primary concern associated with administering calcitriol or its analogues to subjects (e.g. humans or other mammals) is elevated serum calcium (hypercalcemia) and phosphate levels, a condition accompanied by a corresponding increase in urinary calcium excretion (hypercalcuria).

The toxicity of vitamin D compounds can have serious consequences for renal function; prolonged hypercalcemia can result in calcium deposition in the kidneys (nephrocalcinosis), kidney stones (nephrolithiasis), and ultimately in renal dysfunction leading to uremia. Vitamin D intoxication may also have serious consequences for neurological functions. In severe hypercalcemia, the threshold for excitation of nerve and muscles is increased, resulting in clinical manifestations of muscle weakness, lethargy, and even coma. Gastrointestinal manifestations of vitamin D intoxication include constipation, anorexia, nausea, and vomiting, with subsequent fluid loss which exacerbates the hypercalcemic crisis. Hypercalcemia can also affect cardiovascular functioning, including shortening of the QT interval, hypotension, and arrhythmias. Therefore, it is important to monitor the development of hypercalcemia in patients receiving biologically active vitamin D compounds. Hypercalcemia may be monitored in a patient by measuring the terminal serum calcium levels.

One way hypercalcemia risks can be minimized in the treatment of subjects with biologically active vitamin D compounds is by performing dose-response studies in an animal model of IBD (e.g. DS-induced mice, carageenan-induced guinea pigs, or IL-2, TGF-$\beta$1, TCR, MHC, or IL-10 knockout mice) employing a chosen biologically active vitamin D compound. In certain embodiments, these studies involve assaying the level of the biologically active vitamin D compound in the serum and correlating dietary dose of this compound to biologically efficacy and the symptoms of hypercalcemia such that the minimum effective dose is determined. Another method of minimizing the risks of hypercalcemia involves administering the biologically active vitamin D compound using timed drug release methods (e.g. suppository or transdermal patch) or "slow release" biologically active vitamin D derivatives (See, U.S. Pat. No. 5,952,317, hereby incorporated by reference).

While it is not intended that the present invention be limited to a particular mechanism of action, and indeed, an understanding of the mechanism is not necessary to make and use the present invention, it is believed that the use of a transdermal patch reduces the risk of hypercalcemia (caused by mobilization of calcium across the intestinal wall) by preventing a delivery 'spike' of the biologically active vitamin D compound. A transdermal patch is believed to deliver a continuous, lower dosage stream of the biologically active vitamin D compounds such that a spike (total dosage all at once) which could cause a severe increase in the mobilization of calcium across the intestine wall, is avoided.

III. Biologically Active Vitamin D Compounds

As defined above, biologically active vitamin D compounds of the present invention encompass vitamin D compounds which are biologically active in vivo, or are acted upon in a subject (i.e. host) such that the compound becomes active in vivo. Examples of such compounds include: vitamin D, 1,25(OH$_2$)D$_3$ and analogs thereof (e.g. 1$\alpha$-hydroxyvitamin D$_3$ (1$\alpha$-OH-D$_3$), 1,25-dihydroxyvitamin D$_2$ (1,25-(OH)$_2$D$_2$), 1$\alpha$-hydroxyvitamin D$_2$ (1$\alpha$-OH-D$_2$), 26,27-hexafluoro-1,25-dihydroxyvitamin D$_2$ (F$_6$-1,25-(OH)$_2$D$_3$), 19-nor-1,25-dihydroxyvitamin D$_2$ (19-nor-1,25-(OH)$_2$D$_2$), 1,25-dihydroxy-24(E)-dehydro-24-homo-vitamin D$_3$ (1,25-(OH)$_2$-24-homoD$_3$), 19-nor-1,25-dihydroxy-21-epi-vitamin D$_3$ (19-nor-1,25-(OH)$_2$-21-epi-D$_3$), 1$\alpha$,25 dihydroxyvitamin D$_3$ triacetate and 25-acetyl-1$\alpha$,25 dihydroxyvitamin D$_3$, 1,25-dihydroxy-24-homo-22-dehydro-22E-vitamin D$_3$, 19-nor-1,25-dihydroxy-24-homo-22-dehydro-22E-vitamin D$_3$, 1$\alpha$,25-(OH)$_2$-24-epi-D$_2$, 1$\alpha$,25-(OH)$_2$-24a-Homo-D$_3$, 1$\alpha$,25-(OH)$_2$-24a-Dihomo-D$_3$, 1$\alpha$,25-(OH)$_2$-19-nor-D$_3$, and 20-epi-24-homo-1$\alpha$,25-(OH)$_2$-D$_3$). [See, U.S. Pat. Nos. 5,716,946 and 5,891,865, and Bouillon et al., *Endocr Rev.* April;16(2):200–57 (1995), all incorporated herein by reference].

The present invention also contemplates other biologically active vitamin D compounds which may be represented by various functional classes. The first functional class are vitamin D compounds which exhibit significant activity in vivo as inhibitors of autoimmunity (e.g. multiple sclerosis or experimental autoimmune encephalomyelitis, type one diabetes, arthritis or lyme arthritis or collagen-induced arthritis, glomerulonephritis, thyroidits, systemic lupus erythematosis), and which exhibit calcemic activity in vivo that is less than or equal to but not more than calcitriol (i.e. 1,25(OH)$_2$D$_3$. Examples of this class include, but are not limited to, 1α,25-dihydroxy-16ene-vitamin D$_3$ and 1α,25-dihydroxy-24-oxo-16ene-vitamin D$_3$ [See, Lemire et al., *Endocrinology*, 135:2818–2821, (1994)]; 1α,24R-dihydroxy-vitamin D$_3$ [See, Koizumi et al., *Int. Arch. Allergy Appl. Immunol.*, 77:396–404 (1985); 1α,25-dihydroxy-22-oxa-vitamin D$_3$ [See, Abe et al., *Endocrinology*, 124:2645–2647 (1989)]; 20-Epi-22-oxa-24a,26a,27a-trihomo-1α,25-dihydroxy-vitamin D$_3$ [Lillerang et al., *Clin. Exp. Immunol.*, 88:301–306 (1992)]; and 19-nor-1,25-dihydroxy-vitamin D$_3$ [See, U.S. Pat. No. 5,716,946].

The second functional class are vitamin D compounds which exhibit significant activity in vivo as an inhibitor of transplanted cells, tissue, or organ rejection (e.g. skin graft, heart graft, islet graft, etc.), and exhibit calcemic activity in vivo that is less than or equal to calcitriol. Examples of this class include, but are not limited to, 1,25-dihydroxy-16ene-vitamin D$_3$ [See, Lemire et al., *Transplantation*, 54:762–763 (1992)]; and 20-Epi-22-oxa-24a,26a,27a-trihomo-1,25-dihydroxy-vitamin D$_3$ [See, Veyron et al., *Transplant Immunol.*, 1:72–76 (1993)].

The third functional class are vitamin D compounds which exhibit significant activity in an in vitro cell differentiation assay (e.g. HL-60, U-937, NB4, etc.) and exhibit in vivo calcemic activity that is less than or equal to calcitriol. Examples of this class include, but are not limited to 1,25-dihydroxy-16,23E-diene-26-trifluoro-19-nor-cholecalciferol [See, Asou et al., *Blood*, 92:2441–2449 (1998)]; 11α-vinyl-1α,25-dihydroxy-vitamin D$_3$ [See, Bouillon et al., *J. Biol. Chem.*, 267:3044–3051 (1992)]; 1α,25-dihydroxy-16ene-23yne-vitamin D$_3$ [Norman et al., *Cancer Res.*, 50:6857–6864 (1990)]; 24-homo-22-dehydro-22E-1α,25-dihydroxy-vitamin D$_3$ and 1,25-dihydroxy-22ene-24-homo-vitamin D$_3$ [Perlman et al., *Biochemistry*, 29:190–196).

The fourth functional class are vitamin D compounds (mimics) which exhibit significant activity as an activator of the nuclear vitamin D receptor in an in vitro transcriptional activation assay, while also exhibiting a binding affinity for the serum vitamin D binding protein that is less than or equal to calcitriol. An example of this class includes, but is not limited to LG190090, LG190119, LG190155, LG190176, and LG1900178 [See, Boehm et al., *Chemistry & Biology* 6:265–275 (1999)].

Other biologically active vitamin D compounds are contemplated for use in the present invention, including, but not limited to, compounds described in: U.S. Pat. No. 5,936,105 (incorporated herein by reference), U.S. Pat. No. 5,932,565 (incorporated herein by reference), U.S. Pat. No. 5,929,056 (incorporated herein by reference), U.S. Pat. No. 5,905,074 (incorporated herein by reference), U.S. Pat. No. 5,902,806 (incorporated herein by reference), U.S. Pat. No. 5,883,271 (incorporated herein by reference), U.S. Pat. No. 5,877,168 (incorporated herein by reference), U.S. Pat. No. 5,872,140 (incorporated herein by reference), U.S. Pat. No. 5,811,562 (incorporated herein by reference), U.S. Pat. No. 5,786,347 (incorporated herein by reference), U.S. Pat. No. 5,756,733 (incorporated herein by reference), U.S. Pat. No. 5,716,945 (incorporated herein by reference), and U.S. Pat. No. 5,710,142 (herein incorporated by reference). Other biologically active compounds useful in the practice of the present invention are indicated by the following formulas:

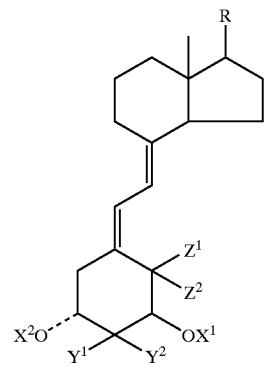

wherein $X^1$ and $X^2$ are each selected from the group consisting of hydrogen and acyl;

wherein $Y^1$ and $Y^2$ can be H, or one can be O-aryl or O-alkyl while the other is hydrogen and can have a β or α configuration; $Z^1$ and $Z^2$ are both H, or $Z^1$ and $Z^2$ taken together are $CH_2$; and wherein R is an alkyl, hydroxyalkyl or fluoroalkyl group, or R may represent the following side chain:

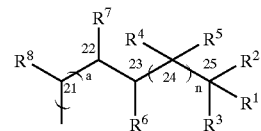

wherein (a) may have an S or R configuration and wherein $R^1$ represents hydrogen, hydroxy or O-acyl, $R^2$ and $R^3$ are each selected from the group consisting of alkyl, hydroxyalkyl and fluoroalkyl, or, when taken together represent the group —$(CH_2)_m$— where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, hydroxy, fluorine, alkyl, hydroxyalkyl and fluoroalkyl, or, $R^4$ and $R^5$ taken together represent double-bonded oxygen, $R^6$ and $R^7$ taken together form a carbon-carbon double bond and $R^8$ may be H or $CH_3$, and wherein n is an integer having a value of from 1 to 5, and wherein the carbon at any one of positions 20, 22, or 23 in the side chain may be replaced by an O, S, or N atom. As used herein, the term "alkyl" signifies an alkyl radical of 1 to 5 carbons in all isomeric forms, such as methyl, ethyl, propyl, isopropyl, butyl, isobutyl, pentyl, etc., and the terms "hydroxyalkyl" and "fluoroalkyl" refer to such an alkyl radical substituted by one or more hydroxy or fluoro groups respectively. The term "acyl" means an aliphatic acyl group of 1 to 5 carbons, such as formyl, acetyl, propionyl, etc. or an aromatic acyl group such as benzoyl, nitrobenzoyl or halobenzoyl. The term "aryl" signifies a phenyl-, or an alkyl-, nitro- or halo-substituted phenyl group.

The present invention also contemplates "slow release" derivatives of the biologically active vitamin D compounds of the present invention (See U.S. Pat. No. 5,952,317, incorporated herein by reference). The following formula describes these various derivatives:

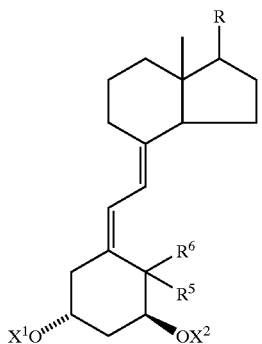

where $R^5$ and $R^6$ each represent hydrogen, or taken together $R^5$ and $R^6$ represent a methylene group.

The side chain group R in the above-shown structure represents a steroid side chain of the structure below:

where the stereochemical center (corresponding to C-20 in steroid numbering) may have the R or S configuration, (i.e., either the natural configuration about carbon 20 or the opposite unnatural configuration), and where Z is selected from Y, —OY, —$CH_2$ OY, —C≡CY and —CH=CHY, where the double bond may have the cis or trans geometry, and where Y is selected from a radical of the structure:

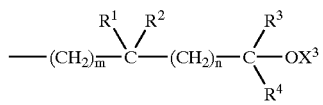

where m and n, independently, represent the integers from 0 to 5, where $R^1$ is selected from hydrogen, $OX^4$, fluoro, trifluoromethyl, and $C_{1-5}$-alkyl, which may be straight chain or branched and, optionally, bear a hydroxy substituent, and where $R^2$ is selected from hydrogen, fluoro, trifluoromethyl and $C_{1-5}$ alkyl, which may be straight-chain or branched, and optionally, bear a hydroxy substituent, and where $R^3$ and $R^4$, independently represent trifluoromethyl or $C_{1-5}$alkyl, which may be straight chain or branched and, optionally, bear a hydroxy substituent, and where $R^1$ and $R^2$, taken together, represent an oxo group, or an alkylidene group, =$CR^2R^2$, or =$CR^2R^3$, or the group —$(CH_2)_p$—, where p is an integer from 2 to 5, and where $R_3$ and $R_4$, taken together, represent the group —$(CH_2)_q$—, where q is an integer from 2 to 5. In the above-shown structures $X^1$, $X^2$ and $X^4$ independently represent hydrogen, an acyl group or a hydrocarbyloxycarbonyl group, and $X^3$ represents an acyl group or a hydrocarbyloxycarbonyl group, as previously defined herein.

In order to evaluate whether a given vitamin D analog or slow release derivative is suitable as a biologically active vitamin D compound useful for the treatment of IBD, an animal model of IBD (e.g. DS-induced mice, carageenan-induced guinea pigs, or IL-2, TGF-β1, TCR, MHC, IL-10 knockout mice, HLA-B27/β2m transgenic rat, trinitrobenzene sulfonic acid induced colitis in rodents, or spontaneous IBD in cotton-top tamarin colonies held in temperate climates) may be employed [See also, Bouillon et al., Endocr Rev. April;16(2):200–57 (1995)]. The inhibition of both induction and established IBD, as well as risk of hypercalcemia are evaluated. Useful biologically active vitamin D compounds reduce the symptoms of IBD. Especially useful biologically active vitamin D compounds reduce the symptoms of IBD, and do not cause substantial hypercalcemia at therapeutic dosages.

IV. Therapeutic Preparations and Combinations

In some embodiments, the present invention contemplates using therapeutic compositions of biologically active vitamin D compounds. It is not intended that the present invention be limited by the particular nature of the therapeutic composition. For example, such compositions can be provided together with physiologically tolerable liquids, gels, solid carriers, diluents, adjuvants and excipients (and combinations thereof).

In addition, biologically active vitamin D compounds may be used together with other therapeutic agents, including, but not limited to, salicylates, steroids, immunosuppressants, antibodies or antibiotics. Particular therapeutic agents which may be used with the biologically active vitamin D compounds of the present invention include, but are not limited to, the following agents: azobenzene compounds (U.S. Pat. No. 4,312,806, incorporated herein by reference), benzyl-substituted rhodamine derivatives (U.S. Pat. No. 5,216,002, incorporated herein by reference), zinc L-carnosine salts (U.S. Pat. No. 5,238,931, incorporated herein by reference), 3-phenyl-5-carboxypyrazoles and isothiazoles (U.S. Pat. No. 5,294,630, incorporated herein by reference), IL-10 (U.S. Pat. No. 5,368,854, incorporated herein by reference), quinoline leukotriene synthesis inhibitors (U.S. Pat. No. 5,391,555, incorporated herein by reference), 2'-halo-2'deoxy adenosine (U.S. Pat. No. 5,506,213, incorporated herein by reference), phenol and benzamide compounds (U.S. Pat. No. 5,552,439, incorporated herein by reference), tributyrin (U.S. Pat. No. 5,569,680, incorporated herein by reference), certain peptides (U.S. Pat. No. 5,756,449, incorporated herein by reference), omega-3 polyunsaturated acids (U.S. Pat. No. 5,792,795, incorporated herein by reference), VLA-4 blockers (U.S. Pat. No. 5,932,214, incorporated herein by reference), prednisolone metasulphobenzoate (U.S. Pat. No. 5,834,021, incorporated herein by reference), cytokine restraining agents (U.S. Pat. No. 5,888,969, incorporated herein by reference), and nicotine (U.S. Pat. No. 5,889,028, incorporated herein by reference).

The therapeutic compositions of the present invention can be administered to mammals for veterinary use, such as with domestic animals and non-human primates, and clinical use in humans in a manner similar to other therapeutic agents. In general, the dosage required for therapeutic efficacy varies according to the type of use and mode of administration, as well as the particularized requirements of individual hosts. A preferred dose of the biologically active vitamin D compounds of the present invention is the maximum that a patient can tolerate and not develop serious hypercalcemia. The attending medical professional is capable of determining the therapeutically effective dosage based on the characteristics of the subject (e.g., gender, age, weight, amount of calcium in diet, etc.).

With respect to the mode of administration, in some embodiments the biologically active vitamin D compounds (and therapeutic compositions thereof) are administered intravenously, intra-muscularly, subcutaneously, intradermally, intraperitoneally, intrapleurally, intrathecally, orally, rectally or topically. In some embodiments, formulations for such administrations may comprise an effective amount of the biologically active vitamin D compound in sterile water or physiological saline. In other embodiments, formulations for such administrations may comprise an effective amount of the biologically active vitamin D compound in an organic solvent (e.g. ethanol, vegetable oil, or glycerol).

On the other hand, therapeutic compositions may contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The biologically active vitamin D compounds of the present invention can also be mixed with diluents or excipients which are compatible and physiologically tolerable. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

In some embodiments, the therapeutic compositions of the present invention are prepared either as liquid solutions or suspensions, as sprays, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%. One example of an oral composition useful for delivering the therapeutic compositions of the present invention is described in U.S. Pat. No. 5,643,602 (incorporated herein by reference).

Additional formulations which are suitable for other modes of administration, such as topical administration, include salves, tinctures, creams, lotions, transdermal patches, and suppositories. For salves and creams, traditional binders, carriers and excipients may include, for example, polyalkylene glycols or triglycerides. One example of a topical delivery method is described in U.S. Pat. No. 5,834,016 (incorporated herein by reference). Other liposomal delivery methods may also be employed. Examples of this type of delivery of the biologically active vitamin D compounds of the present invention include U.S. Pat. Nos. 5,851,548 and 5,711,964 (both incorporated herein by reference).

In certain particularly preferred embodiments, the therapeutic composition comprising biologically active vitamin D compounds is administered via a transdermal patch. A transdermal patch optimally includes a therapeutically effective amount of the biologically active vitamin D compounds of the present invention. While not limited to any mechanism, it is believed that transdermal delivery would provide a continuous supply of the vitamin D compound, maintaining the vitamin D receptor occupancy at a stable, optimal level, to achieve the desired biological effect. This is in contrast to other modes of delivery (e.g. oral or intravenous) which could provide a peak hormone concentration (spike) shortly after delivery, which would subsequently decline (leading to cyclical hormone occupancy and peak concentrations stimulating calcium absorption, bone resorption, or soft tissue calcification). Transdermal delivery may also bypass delivery of the vitamin D compounds to the intestine, decreasing binding to the vitamin D receptors in the intestinal epithelial cells. This in turn may decrease stimulation of intestinal calcium absorption, and decrease the calcemic effect of the vitamin D compound. Transdermal delivery may also be preferred because intestinal physiology is disturbed in patients with IBD, which may alter uptake of the vitamin D compound in a patient-specific, non-predictable manner (making dose determination difficult for other modes of administration such as oral delivery). Transdermal delivery may be more convenient than other modes of delivery (especially for children), and could increase patient compliance.

One example of a transdermal patch for delivering therapeutics employs a polyurethane acrylic copolymer (U.S. Pat. No. 4,638,043, incorporated herein by reference). Another example of a transdermal patch employs polymers and vitamin E (U.S. Pat. No. 5,830,505, incorporated herein by reference). A third example of a transdermal patch employs an adhesive matrix of silicone or polyisobutylene or both (U.S. Pat. No. 5,876,746, incorporated herein by reference). Other transdermal patches are known in the art, and are contemplated as modes for delivering the biologically active vitamin D compounds of the present invention.

In other preferred embodiments, enteric formulations are employed. The covering may comprise an enteric coating or a capsule. The terms "enteric coating" or "enteric film" are used interchangeably and refer to a material or compound which is resistant to acid pH (i.e., an acid-resistant compound), such as that found in the stomach. An enteric coating when applied to a solid inhibits the dissolution of the solid in the stomach.

Standard techniques are known to the art for the encapsulation of solid compositions. These techniques include microencapsulation of a solid composition wherein an enteric coating is applied to the solid composition. The coated material may be delivered orally to a subject by suspending the microencapsulated particles in pharmaceutical suspension solutions known to the art. The capsule would preferably have the characteristic of being resistant to dissolution in the stomach and being capable of dissolving in the intestines. Numerous suitable capsule formulations are available to the art; in addition standard techniques are available for the filling of capsules including the use of inert filler materials to provide sufficient bulk of the filling of a capsule with a therapeutic composition in a solid form. In addition to the use of encapsulated compositions, the biologically active vitamin D compounds may be delivered orally in tablet or pill form. The biologically active vitamin D compounds may be combined with inert materials to provide sufficient bulk for the pressing of the tablet or pill. Once formed, the tablet or pill may then be coated with an enteric film to prevent dissolution in the stomach and to enhance dissolution in the intestines.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); $\mu$M (micromolar); mol (moles); mmol (millimoles); μmol (micromoles); nmol (nanomoles); pmol (picomoles); g (grams); mg (milligrams); ug (micrograms); ng (nanograms); l or L (liters); ml (milliliters); μl (microliters); cm (centimeters); mm (millimeters); μm (micrometers); nm (nanometers); DS (dextran sulfate); ° C. (degrees Centigrade); Sigma (Sigma Chemical Co., St. Louis, Mo.); and

EXAMPLE 1

Calcitriol Inhibition of IBD Induction

This Example describes the inhibition of IBD induction in mice with calcitriol. Two types of mouse models are utilized. The fist group is the widely used DS-induced murine model, which reflects the involvement of enteric microbes, innate immunity, and non-specific inflammation in IBD. Mouse strains vary in their susceptibility to DS-induced IBD [Mahler et al., Am. J. Physiol.—Gastro. & Liver Physiol., 37 G: 544-G 551, (1998)], so the highly susceptible strains C3H/HeJ and C57BL/6J are employed. The second group of IBD models involves mice with targeted disruptions in immunologically relevant genes. In particular, the widely used IL-10 knockout on the C57BL/6J background is employed (i.e. C57BL/6J-IL-10 ko). An alternative to these C57BL/6J-IL-10 ko mice (not described in this Experiment), are mice with a homozygous IL-10 ko mutation on the mixed 129/Ola×C57BL/6 genetic background. These two groups of mice are employed as described below to demonstrate the effect of calcitriol on the inhibition of IBD induction (See Table 1, overview of Experimental Groups).

TABLE 1

Experimental Groups.

| Group | Strain | Inducing agent | Treatment |
|---|---|---|---|
| 1 | C3H/HeJ | none | none |
| 2 | C3H/HeJ | DS | none |
| 3 | C3H/HeJ | DS | calcitriol |
| 4 | C3H/HeJ | DS | prednisolone |
| 5 | C57BL/6J | none | none |
| 6 | C57BL/6J | DS | none |
| 7 | C57BL/6J | DS | calcitriol |
| 8 | C57BL/6J | DS | prednisolone |
| 9 | 129/O1a × C57B1/6J-IL-10 ko | none | none |
| 10 | 129/O1a × C57BL/6J-IL-10 ko | none | calcitriol |
| 11 | 129/O1a × C57BL/6J-IL-10 ko | none | prednisolone |

A. Treatment of the Mice

The DS-induced IBD study (groups 1–8; Table 1) are treated as follows. Beginning on day 0 and continuing, groups of 10 mice are fed a purified diet without or with calcitriol (50 ng/day females; 200 ng/day males); this dose is based on dose-response studies in EAE [Cantoma et al., J. Immunol., 160:5314–5319 (1998)]. The prednisolone-treated group is fed a purified diet with prednisolone (20 ng/day). These experimental diets have been published [Cantoma et al., Proc. Natl. Acad. Sci. USA, 97:7861–7864 (1996)], and are replenished each 2–3 days. On day 2, the mice are weighed and DS (3.5% wt/vol) is given in the drinking water on days 2–6 (Okayasu, et al., Gastro., 98:694–702 (1990)]. The mice receive acidified drinking water without DS for days 7–22. On days 7, 11, 15, and 19, mice are weighed and stool samples are collected. A blood sample is collected on day 11. On day 22, mice are weighed, euthanized, and stool, blood, and colon samples are collected. The samples are analyzed as described below.

The mock-treated control mice in this Example are expected to show severe weight loss, bloody diarrhea (as evidenced by fecal hemoglobin), shortening of the colon and thickening of the colonic wall, mucosal ulceration, goblet cell loss, and crypt elongation and loss (as evidenced by histopathologic score), and inflammatory infiltration by lymphocytes, macrophages, neutrophils, and granulocytes (as evidenced by fecal lactoferrin and colonic myeloperoxidase activity) during IBD induction and progression. The calcitriol-treated mice exhibit significantly reduced incidence or severity of disease as compared to the mock-treated controls. With respect to severity, the calcitriol-treated mice exhibit significantly reduced weight loss, bloody diarrhea, shortening and thickening of the colon, histopathologic score, and inflammatory infiltration as compared to the mock-treated controls.

The spontaneous IBD study (groups 9–11; Table 1) are treated the same as the DS-induced mice, except purified diet feeding begins when the IL-10-ko mice are weaned at age 3 weeks, and no DS is administered. Mice are weighed and stool samples are collected twice weekly for four weeks. A blood sample is collected at age 5 weeks. After four weeks, mice are weighed, euthanized, and stool, blood, and colon samples are collected. These samples are analyzed as described below in Example 2.

The mock-treated control mice carrying a null-mutation of the IL-10 gene described in this Example are expected to show growth retardation by age 4 weeks (as evidenced by low blood hemoglobin levels), and a significant mortality incidence by 10 weeks. These mice are also expected to show clinical signs of IBD, specifically bloody fecal lactoferrin and colonic myeloperoxidase activity, perianal ulceration, and occasional rectal prolapse. Finally, these mice are expected to show histopathological signs of IBD, specifically inflammatory infiltration with lymphocytes, plasma cells, marcophages, and neutrophils, ulceration, abnormal enlarged and branched crypts, branched and fused villus structures, and marked hyperplasia of the mucosa leading to thickening of the intestinal wall. The calcitriol-treated mice exhibit significantly reduced growth retardation, anemia, mortality, bloody diarrhea, intestinal inflammation, perianal ulceration and rectal prolapse, and histopathologic score as compared to the mock-treated controls.

EXAMPLE 2

Analysis of Samples from Treated Mice

This Example describes the analysis of stool, serum, and colon samples from both groups of mice described in Example 1. Stool extracts are analyzed individually for protein, hemoglobin, and lactoferrin. Serum samples are analyzed for Ca, IFN-γ, and TGF-β1. Colon samples are analyzed individually for myeloperoxidase (5/group), IFN-γ and TGF-β1 immunohistochemistry, and for histopathology (5/group). Fecal extracts and intestinal tissue extracts are assayed for protein content by a micro-Bradford assay [Bradford, M. M., Anal. Biochem., 72:248–254 (1976)]. Results of the hemoglobin, lactoferrin, and myeloperoxidase assays are then determined per mg of protein in the sample. Fecal hemoglobin and fecal lactoferrin (as well as weight) are plotted as a function of time. Histopathology scores for disease incidence and severity, myeloperoxidase activity, and IFN-γ and TGF-β1 values are tabulated, and differences between groups are compared by the nonparametric Wilcoxon test (Schefler, W. C., Statistics for the Biological Sciences, 2nd Edition, Addison-Wesley Pub. Co., Reading, Mass., USA, 1979).

A. Stool Sample Assays

Intestinal bleeding in a breached intestinal barrier is measured in live animals by measuring fecal hemoglobin levels, which have been shown to be elevated in UC patients [Saitoh, et al., *Digestion* 56:67–75 (1995)]. Stool samples, collected over a 24 hour period are weighed, homogenized in a small amount of water, and centrifuged in order to detect the relative hemoglobin concentration of each sample (ng/mg of protein).

The fecal hemoglobin two-site ELISA is performed on these samples as described [Saitoh, et al., *Digestion*, 56:67–75 (1995)] with modifications. All ELISA steps are separated by washing four times (TRIS-buffered saline with 0.05% Tween 20). ELISA plates (Immulon, Dynatech; 96-well) are coated overnight in the cold with rabbit polyclonal antibodies (pAb) to mouse hemoglobin (ICN Biomedical Research Products; 5 µg/ml in 0.1 M sodium carbonate buffer pH 8.2), and blocked with 0.1 M TRIS-buffered saline (pH 8) containing 1% bovine serum albumin. The samples and the hemoglobin standard (Sigma) are serially diluted in buffer (0.1 M TRIS-buffered saline, pH 7.5, with 0.1% bovine serum albumin) and aliquots are incubated 1 hour at 37° C. in duplicate assay wells; assay blank wells receive buffer only. An optimal amount of biotinylated rabbit pAb to mouse hemoglobin (ICN) is added to each well and incubated 1 hour at 37° C. The assay is developed with tetramethylbenzidine (TMB) plus hydrogen peroxide substrate solution (ICN), the reaction is stopped by adding 100 µl of 1M phosphoric acid, and the color is measured on an ELISA plate reader. The hemoglobin in each sample is determined from the linear portion of a log-linear plot of A-450 nm versus hemoglobin standard concentration, and results are expressed in ng/mg protein. The calcitriol-treated mice exhibit less hemoglobin protein in stool extracts than the mock-treated control mice.

GI tract inflammation in live animals is indicated by measuring fecal lactoferrin concentrations. High levels of fecal lactoferrin have been demonstrated in patients with colorectal diseases [Sugi et al., *Am. J. Gastroenterol.* 91:927 (1996)]. The fecal lactoferrin two-site ELISA is performed in the same manner as the hemoglobin assay above, except that rabbit pAb to human lactoferrin (ICN Biomedical Research Products) replaces rabbit pAb to mouse hemoglobin as the coating Ab, and biotinylated rabbit pAb to human lactoferrin replaces rabbit pAb to mouse hemoglobin as the detecting Ab. The lactoferrin in each sample is determined from the linear portion of a log-linear plot of A-450 nm versus lactoferrin standard concentration. Results are expressed as lactoferrin ng/mg protein. The calcitriol-treated mice show less lactoferrin protein in stool extracts than the mock-treated control mice.

B. Colon Tissue Assays

Large intestine of the euthenized mice are collected, and the cecum is separated from the colon. Intestinal specimens are gently flushed with Fekete's acid-alcohol-formalin fixative. The entire colon, including the rectum, is prepared as an intestinal roll [Moolenbeek and Ruitenber, *Lab Anim.* 15:57–59 (1981)]. It is placed on an index card and rolled into concentric centrifugal circles (in the plane of the card) around a central toothpick. Intestinal rolls are fixed overnight in Fekete's solution, and then transferred to 70% ethanol. The fixed intestinal rolls are then embedded in paraffin, sectioned at 5 µm, and stained with hematoxylin and eosin.

Two intestinal role sections per animal are coded and evaluated by a veterinary pathologist and a researcher without access to the code. A published evaluation method is used [Mahler et al., *Am. J. Physiol.—Gastro. & Liver Physiol.*, 37 G: 544-G 551, (1998)]. The evaluation is based on severity of lesions (graded 0 to 3), and estimated area involved (graded 0 to 4). The severity, ulceration, hyperplasia, and affected area scores are summed and tabulated, with the calcitriol-treated mice exhibiting a lower histopathological score than the mock-treated mice.

Myeloperoxidase assays have been used as objective and quantitative measures of inflammation in humans [e.g. Dwarakanath et al., *Clin. Sci.* 92:307–13 (1997)] and animals [e.g. Hogaboam et al., *J. Clin. Invest.*, 100:2766–76 (1997)] with IBD. Accordingly, intestinal inflammation is measured in the mouse intestinal tissue samples by measuring myeloperoxidase activity levels. The myeloperoxidase assay is performed as in Krawisz et al., *Gastroenterol.* 87:1344–50 (1984), as modified by Schneider and Issekutz, *J. Immunol. Methods*, 198:1–14 (1996). Briefly, washed intestinal tissue samples (3/mouse; 200 mg each) are minced and homogenized in hexadecyltrimethylammonium bromide (HTAB) buffer (1 ml; 0.5% HTAB in 50 mM phosphate, pH 6) to release the enzyme. The homogenate is frozen and thawed four times, then centrifuged. The supernatant (10 µl) is added to a well of a 96-well plate containing 0.29 ml assay mix (TMB plus hydrogen peroxide substrate solution; ICN), and the A-450 nm is measured on an ELISA plate reader as a function of time. An assay blank is prepared with a heat-inactivated supernatant and subtracted. A unit of enzyme activity is defined as the amount catalyzing the oxidation of 1 µmole substrate/min under these conditions. Results are expressed as myeloperoxidase U/mg protein. The calcitriol-treated mice show less myeloperoxidase protein in the intestinal tissue extracts than the mock-treated control mice.

Intestinal tissue is also analyzed for the presence of IFN-γ and TGF-β1 (cytokines thought to regulate mucosal inflammation, see below). Intestinal tissue specimens are snap frozen in OCT embedding compound (Miles Laboratories). Longitudinal 10 µm sections are applied to coated glass slides, air dried, and fixed briefly in acetone. Sections are then re-hydrated in PBS with 0.05% Tween 20, and washed in this buffer between each subsequent reaction step. All reactants are dissolved in PBS-Tween buffer. Sections are reacted 30 minutes with 3% hydrogen peroxide, then 10 minutes with 3% goat serum, then overnight in the cold with polyclonal rabbit antibodies to IFN-γ and TGF-β1 or control rabbit serum, and finally with biotinylated goat antibodies to rabbit IgG. Color is developed with the Vector Elite ABC kit. The intestinal tissue sections from the calcitriol-treated mice exhibit qualitatively greater immunohistochemical staining with polyclonal rabbit antibodies to TGF-β1 and qualitatively less immunohistochemical staining with the polyclonal rabbit antibodies to IFN-γ than the intestinal tissue sections from the mock-treated control mice.

C. Blood and Serum Sample Assays

Anemia can be a sign of IBD due to blood loss in the stool. To determine whether anemia is present, 0.5 ml of blood is obtained on days 11 and 22 (prevention of DS-induced mouse IBD models) and at age 5 and 7 weeks (prevention of spontaneous mouse IBD model). A blood hemoglobin determination is performed. A small blood aliquot is dispensed into lysis buffer [3 mM $K_3(FeCN)_6$, 1.5 mM KCN, 5 mM $Na_2BO_4$, 0.1% Nonidet P-40] and the absorbance at 546 nm is measured using lysis buffer as a blank. This absorbance is compared to a reference curve produced using purified moused hemoglobin dissolved in lysis buffer. The remaining blood is allowed to clot overnight in the cold, centrifuged, and the serum is collected for further analysis.

As hypercalcemia is a possible serious side-effect of calcitriol administration [Chan et al., *Cur. Prob. Surgery*, 34:445–523 (1997)], calcitriol-treated and control mice are monitored for terminal serum calcium. Serum calcium is measured by a colormetric reaction (Sigma Diagnostics). Calcium ions form a purple complex with o-cresolphthalein complexone at alkaline pH (0.5 M 2-amino-2-methyl-1,3-propanediol buffer); 8-hydroxyquinoline (0.25%) is included to prevent magnesium ion interference. Sample, standard, or buffer blank (10 µl) is added to duplicate tubes of a working solution (1 ml) of equal parts Ca binding reagent and Ca buffer. After 5 minutes, 0.3 ml of each reaction is transferred into a 96-well plate and the absorbance at 575 nm is measured on an ELISA plate reader. Results of this assay aid in the determination the proper level and time course of calcitriol administration to avoid hypercalcemia for subjects treated for IBD with calcitriol.

In previous studies, administration of calcitriol to mice with EAE arrested the clonal expansion of Th1 cells producing IFN-$\gamma$, and stimulated TGF-$\alpha$1 transcript synthesis in the central nervous system and draining lymph nodes [Cantorna et al., *J. Immunol.*, 160:5314–5319 (1998)]. Reciprocal IFN-$\gamma$ and TGF-$\beta$1 responses are thought to regulate mucosal inflammation [Strober et al., *Immunol. Today*, Feb;18(2):61–4 (1997)], and TGF-$\beta$1 responses are crucial to suppress inflammatory colitis [Powrie et al., *J. Exp. Med.*, 183:2669–74 (1996)]. As such, a two-step ELISA is performed to analyze IFN-$\gamma$ (PharMingen) and TGF-$\beta$1 (Promega Corp.) as immune response markers in the serum of the calcitriol-treated mice compared to mock-treated mice.

EXAMPLE 3

Treating Established IBD in Mice

This example describes the treatment of established IBD in mice using calcitriol. The procedure is the same as Example 1 above, except treatment is not started until the mice show signs of IBD. This is accomplished by administering DS in the drinking water of the mice listed in groups 1–4 in Table 1, followed by acidified water without DS thereafter. The mice are also weighed at the beginning of this procedure. At two-day intervals, stool samples are tested as in Example 1 for hemoglobin and lactoferrin. Treatment with calcitriol is begun when these test indicate the mice are suffering from IBD.

Thereafter, weights and stool samples are obtained at 4-day intervals. On day 22, the mice are weighed, euthanized, and stool, blood, and colon samples are collected. Stool extracts, blood, serum, and colon samples are analyzed as described in above in Example 2. Weight, fecal and blood hemoglobin, and fecal lactoferrin are plotted as a function of time. Disease incidence, severity (as evidenced by histopathologic score), myeloperoxidase activity, and IFN-$\gamma$ and TGF-$\beta$1 values are then tabulated. The results of this experiment indicate that calcitriol treatment of mice exhibiting symptoms of IBD exhibit reduced symptoms of disease compared to controls.

EXAMPLE 4

Therapeutic and Prophylactic Use of Calcitriol to Treat and Prevent IBD

Therapeutic formulations of calcitriol are used prophylactically and therapeutically to treat IBD in humans. Individuals at risk of contracting IBD, particularly young adults, or those or Jewish descent are administered an effective amount of calcitriol in a therapeutic formulation to prevent or reduce the severity of the disease. A patient with symptoms of IBD is administered an effective dose of calcitriol daily until symptoms of IBD are reduced.

EXAMPLE 5

Therapetic and Prophylactic Use of Vitamin D to Treat and Prevent IBD

Therapeutic formulations of vitamin D are used prophylactically and therapeutically to treat IBD in humans. Individuals at risk of contracting IBD, particularly young adults, or those or Jewish descent are administered an effective amount of vitamin D in a therapeutic formulation to prevent or reduce the severity of the disease. A patient with symptoms of IBD is administered an effective dose of vitamin D daily until symptoms of IBD are reduced.

All publications and patents mentioned in the above specification are herein incorporated by reference. Various modifications and variations of the described method and system of the invention will be apparent to those skilled in the art without departing from the scope and spirit of the invention. Although the invention has been described in connection with certain preferred embodiments, it should be understood that the invention as claimed should not be unduly limited to such embodiments. Indeed, various modifications of the described modes for carrying out the invention which are obvious to those skilled in biochemistry, immunology, chemistry, molecular biology, the medical profession or related fields are intended to be within the scope of the following claims.

What is claimed is:

1. A method of treating inflammatory bowel disease, comprising:

administering a therapeutically effective amount of a therapeutic composition comprising 1$\alpha$-hydroxyvitamin $D_2$ to a subject suffering from the symptoms of inflammatory bowel disease, wherein said inflammatory bowel disease is selected from the group consisting of ulcerative colitis and Crohn's disease.

2. The method of claim 1, wherein said therapeutically effective amount comprises a daily dose of between 0.1 µg and 20 µg per 160 pounds of said subject.

3. The method of claim 1, wherein said therapeutically effective amount comprises a daily dose of between 0.5 µg and 10 µg per 160 pounds of said subject.

4. The method of claim 1, wherein said therapeutically effective amount comprises a daily dose of between 3.0 µg and 10 µg per 160 pounds of said subject.

5. The method of claim 1, wherein said administering is conducted in a continuous manner.

6. The method of claim 1, wherein said administering is via a transdermal patch.

7. The method of claim 1, wherein said administering is via a suppository.

8. The method of claim 1, wherein said administering is via a slow release oral formulation.

9. A method of treating inflammatory bowel disease, comprising:

administering a therapeutically effective amount of a therapeutic composition comprising 19-nor-1,25-dihydroxyvitamin $D_2$ to a subject suffering from the symptoms of inflammatory bowel disease, wherein said inflammatory bowel disease is selected from the group consisting of ulcerative colitis and Crohn's disease.

10. The method of claim 9, wherein said therapeutically effective amount comprises a daily dose of between 0.1 µg and 20 µg per 160 pounds of said subject.

11. The method of claim 9, wherein said therapeutically effective amount comprises a daily dose of between 0.5 µg and 10 µg per 160 pounds of said subject.

12. The method of claim 9, wherein said therapeutically effective amount comprises a daily dose of between 3.0 µg and 10 µg per 160 pounds of said subject.

13. The method of claim 9, wherein said administering is conducted in a continuous manner.

14. The method of claim 9, wherein said administering is via a transdermal patch.

15. The method of claim 9, wherein said administering is via a suppository.

16. The method of claim 9, wherein said administering is via a slow release oral formulation.

* * * * *

UNITED STATES PATENT AND TRADEMARK OFFICE
CERTIFICATE OF CORRECTION

PATENT NO. : 6,858,595 B2
DATED : February 22, 2005
INVENTOR(S) : Colleen E. Hayes and Faye E. Nashold It is certified that error appears in the above-identified patent and that said Letters Patent is hereby corrected as shown below:

Column 3,
Line 14, "$1\alpha,25(OH)_{2-22}$-oxa-$D_3$," should be -- $1\alpha,25(OH)_2$-22-oxa-$D_3$, --.
Line 15, "$_{20}$-epi-22-oxa-24a," should be -- 20-epi-22-oxa-24a, --.

Column 5,
Line 50, "$X^1$ and $X^1$" should be -- $X^1$ and $X^2$ --.

Column 6,
Lines 26 and 27, "$\alpha,25$-$(OH)_2$-24a-Homo-$D_3$," should be
-- $1\alpha,25$-$(OH)_2$-24a-Homo-$D_3$, --.

Column 23,
Line 23, "TGF-$\alpha1$" should be -- TGF-$\beta1$ --.

Signed and Sealed this

Fourteenth Day of March, 2006

JON W. DUDAS
*Director of the United States Patent and Trademark Office*